US006736823B2

(12) United States Patent
Darois et al.

(10) Patent No.: US 6,736,823 B2
(45) Date of Patent: May 18, 2004

(54) PROSTHETIC REPAIR FABRIC

(75) Inventors: Roger E. Darois, Foster, RI (US);
Stephen N. Eldridge, Exeter, RI (US);
Michael J. Lee, Barrington, RI (US)

(73) Assignee: C.R. Bard, Inc., Murray Hill, NJ (US)

( * ) Notice: Subject to any disclaimer, the term of this patent is extended or adjusted under 35 U.S.C. 154(b) by 0 days.

(21) Appl. No.: 10/143,564

(22) Filed: May 10, 2002

(65) Prior Publication Data

US 2003/0212460 A1 Nov. 13, 2003

(51) Int. Cl.$^7$ .................................................. A61F 2/02
(52) U.S. Cl. ........................ 606/151; 623/23.72; 600/37
(58) Field of Search ........................... 623/23.72, 23.74, 623/23.76; 606/151, 155; 600/37

(56) References Cited

U.S. PATENT DOCUMENTS

| | | |
|---|---|---|
| 2,671,444 A | 3/1954 | Pease |
| 3,875,928 A | 4/1975 | Angelchik |
| 4,271,827 A | 6/1981 | Angelchik |
| 4,403,604 A | 9/1983 | Wilkinson et al. |
| 4,769,038 A | 9/1988 | Bendavid et al. |
| 4,796,603 A | 1/1989 | Dahlke et al. |
| 4,854,316 A | 8/1989 | Davis |
| 5,006,106 A | 4/1991 | Angelchik |
| 5,116,357 A | 5/1992 | Eberbach |
| 5,246,456 A | 9/1993 | Wilkinson |
| 5,258,000 A | 11/1993 | Gianturco |
| 5,290,217 A | 3/1994 | Campos |
| 5,314,473 A | 5/1994 | Godin |
| 5,316,543 A | 5/1994 | Eberbach |
| 5,368,602 A | 11/1994 | de la Torre |
| 5,370,650 A | 12/1994 | Tovey et al. |
| 5,397,332 A | 3/1995 | Kammerer et al. |
| 5,433,996 A | 7/1995 | Kranzler et al. |
| 5,456,720 A | 10/1995 | Schultz et al. |
| 5,480,436 A | 1/1996 | Bakker et al. |
| 5,508,036 A | 4/1996 | Bakker et al. |
| 5,571,116 A | 11/1996 | Bolanos et al. |

(List continued on next page.)

FOREIGN PATENT DOCUMENTS

| | | |
|---|---|---|
| EP | 0 719 527 A1 | 7/1996 |
| EP | 0 898 944 A2 | 3/1999 |

(List continued on next page.)

OTHER PUBLICATIONS

"Bard EndoCinch Introducing Bard's EndoCinch™ Endoscopic Suturing System," http://www.bardendoscopy.com/gerd.htm (Oct. 2001), 7 pages.

(List continued on next page.)

*Primary Examiner*—Bruce Snow
(74) *Attorney, Agent, or Firm*—Wolf, Greenfield & Sacks, P.C.

(57) ABSTRACT

An implantable prosthesis is provided for repairing or augmenting anatomical weaknesses or defects, and is particularly suitable for the repair of soft tissue and muscle wall openings. The prosthesis is configured to promote enhanced tissue ingrowth thereto, while limiting the incidence of post-operative adhesions between the fabric and tissue or organs. The prosthesis may include a layer of fabric that is constructed and arranged to allow tissue ingrowth and is susceptible to the formation of adhesions for tissue and organs. One or more barriers may be provided on selected portions of the fabric to inhibit the formation of adhesions with tissues and organs. The prosthesis may have an opening that is adapted to receive the esophagus or other tube-like structure, or other projection, that passes through an opening in or projects from a tissue, muscle or organ wall requiring repair and/or augmentation. The prosthesis may be configured for use in hiatal hernia repair and/or treatment of GERD. A method is also provided for the treatment of GERD.

96 Claims, 17 Drawing Sheets

U.S. PATENT DOCUMENTS

| | | | |
|---|---|---|---|
| 5,593,441 | A | 1/1997 | Lichtenstein et al. |
| 5,601,579 | A | 2/1997 | Semertzides |
| 5,634,931 | A | 6/1997 | Kugel |
| 5,676,674 | A | 10/1997 | Bolanos et al. |
| 5,695,525 | A | 12/1997 | Mulhauser et al. |
| 5,697,978 | A | 12/1997 | Sgro |
| 5,702,416 | A | 12/1997 | Kieturakis et al. |
| 5,716,409 | A | 2/1998 | Debbas |
| 5,725,577 | A | 3/1998 | Saxon |
| 5,743,917 | A | 4/1998 | Saxon |
| 5,766,246 | A | 6/1998 | Mulhauser et al. |
| 5,769,864 | A | 6/1998 | Kugel |
| 5,836,961 | A | 11/1998 | Kieturakis et al. |
| 5,861,036 | A | 1/1999 | Godin |
| 5,887,594 | A | 3/1999 | LoCicero, III |
| 5,897,562 | A | 4/1999 | Bolanos et al. |
| 5,916,225 | A | 6/1999 | Kugel |
| 5,919,232 | A * | 7/1999 | Chaffringeon et al. ........ 623/11 |
| 5,919,233 | A | 7/1999 | Knopf et al. |
| 5,948,020 | A | 9/1999 | Yoon et al. |
| 5,954,767 | A | 9/1999 | Pajotin et al. |
| 6,066,777 | A | 5/2000 | Benchetrit |
| 6,067,991 | A | 5/2000 | Forsell |
| 6,090,116 | A | 7/2000 | D'Aversa et al. |
| 6,113,623 | A | 9/2000 | Sgro |
| 6,120,539 | A | 9/2000 | Eldridge et al. |
| 6,174,320 | B1 | 1/2001 | Kugel et al. |
| 6,214,020 | B1 | 4/2001 | Mulhauser et al. |
| 6,224,616 | B1 | 5/2001 | Kugel |
| 6,258,124 | B1 | 7/2001 | Darois et al. |
| 6,270,530 | B1 | 8/2001 | Eldridge et al. |
| 6,280,453 | B1 | 8/2001 | Kugel et al. |
| 6,287,316 | B1 | 9/2001 | Agarwal et al. |
| 6,290,708 | B1 | 9/2001 | Kugel et al. |
| 6,319,264 | B1 | 11/2001 | Tormala et al. |
| 6,383,201 | B1 | 5/2002 | Dong |
| 6,497,650 | B1 * | 12/2002 | Nicolo ........................ 600/37 |
| 6,551,356 | B2 * | 4/2003 | Rousseau ................. 623/23.72 |
| 6,596,002 | B2 * | 7/2003 | Therin et al. ............... 606/151 |
| 2001/0049539 | A1 | 12/2001 | Rehil |
| 2002/0001609 | A1 | 1/2002 | Calhoun et al. |
| 2002/0013590 | A1 | 1/2002 | Therin et al. |
| 2002/0042658 | A1 | 4/2002 | Tyagi |
| 2002/0052654 | A1 | 5/2002 | Darois et al. |

FOREIGN PATENT DOCUMENTS

| | | |
|---|---|---|
| EP | 0 898 944 A3 | 8/1999 |
| FR | 2145975 | 2/1973 |
| FR | 2744906 A1 | 8/1997 |
| GB | 1 406 271 | 9/1995 |
| WO | WO 97/35533 | 10/1997 |
| WO | WO 99/56664 | 11/1999 |
| WO | WO 00/07520 A1 | 2/2000 |
| WO | WO 00/42943 | 7/2000 |
| WO | WO 01/08594 A1 | 2/2001 |
| WO | WO 01/54589 A1 | 8/2001 |
| WO | WO 01/81667 A1 | 11/2001 |
| WO | WO 01/85058 A2 | 11/2001 |
| WO | WO 02/22047 A1 | 3/2002 |

OTHER PUBLICATIONS

Basso et al., "360° Laparoscopic Fundoplication With Tension-Free Hiatoplasty in The Treatment of Symptomatic Gastreoesophageal Reflux Disease," 14 *Surg. Endosc.* 164–169 (2000).

Carlson et al., "Management of Intrathoracic Stomach With Polypropylene Mesh Prosthesis Reinforced Transabdominal Hiatus Hernia Repair," 187(3) *J. Am. Coll. Surg.* 227–230 (1998).

Carlson et al., "Laparoscopic Prosthetic Reinforcement of Hiatal Herniorrhaphy," 16 *Dig. Surg.* 407–410 (1999).

Carlson et al., "Polypropylene Mesh Reinforced Hiatus Hernia Repair," 112(4) *Gastroentology* (Apr. 1997).

Carugno et al., "Development of an Adjustable Prosthesis For The Treatment of Gastroesophageal Reflux," 44 *ASAIO Journal* 140–143 (1998).

Frantzides et al., "Laparoscopic Repair of Large Hiatal Hernia With Polytetrafluoroethylene," 13 *Surg. Endosc.* 906–908 (1999).

Frantzides et al., "Prosthetic Reinforcement of Posterior Cruroplasty During Laparoscopic Hiatal Herniorrhaphy," 11 *Surg. Endosc.* 769–771 (1997).

Huntington, "The Surgeon at Work: Laparoscopic Mesh Repair of The Esophageal Hiatus," 184 *J. Am. Coll. Surg.* 399–400 (Apr. 1997).

Kennedy, "Hiatus Hernia Repair Clinical and Radiological Results of a New Combined Thoracoabdominal Technique," 1 *Med. J. Australia* 386–390 (1974).

Kozarek et al., "Evaluation of Angelchik Antireflux Prosthesis: Long Term Results", 30(8) *Digestive Diseases and Sciences* 723–732 (Aug. 1985).

Lees et al., "Esophageal Perforation: A Complication of The Angelchik Prosthesis," 50(4) *Cleve. Clin. Q.* 449–451 (1983).

Patel et al., "Angelchik Antireflux Prosthesis—Its Usefulness And Review of Literature," 79(1) *Am. J. of Gastroenterology* 12–15 (1984).

Sakashita et al., "Repair of Posttraumatic and Recurrent Diaphragm Hernias With Prosthetic Mesh," 15(1) *Acta Medica et Biologica* 1–14 (1967).

Thibault et al., "The Angelchik Antireflux Prosthesis: Long–Term Clinical and Technical Follow–up," 37(1) *Canadian J. Surg.* 12–17 (Feb. 1994).

Waldhausen et al., "The Diagnosis and Management of Traumatic Injuries of the Diaphragm Including The Use of Marlex Prostheses," 6(3) *J. of Trauma* 332–343 (1966).

Watanabe et al., "Laparoscopic Repair of a Paraesophageal Hiatus Hernia Without Fundoplication," 27 *Surgery Today* 1093–1096 (1997).

Simpson et al., "Prosthetic Patch Stablization of Crural Repair in Antireflux Surgery in Children," *The American Surgeon*, Jan. 1998, pp. 67–69, vol. 64.

Paul, et al., "Laparoscopic tension–free repair of large paraesophageal hernias", *Surg Endosc.*, 1997, pp. 303–307, vol. 11.

Edelman, David S., M.D., "Laparascopic Paresophageal Hernia Repair with Mesh", *Surgical Laparascopy & Endoscopy*, 1995, pp 32–37, vol. 5, No. 1.

Champion et al., "Laparascopic Mesh Cruroplasty for Large Paraeosphageal Hernias," *Surgical Endoscopy and Other Interventional Techniques*, Feb. 17, 2003, pp. 551–553, vol. 17, No. 4.

* cited by examiner

PROSTHETIC REPAIR FABRIC

FIELD OF THE INVENTION

The present invention relates to an implantable prosthesis, and more particularly to a prosthetic repair fabric for use in soft tissue repair and reconstruction.

DISCUSSION OF RELATED ART

Gastroesophageal reflux disease ("GERD") and hiatal hernia commonly occur together. A hiatal hernia occurs when a natural opening, or "hiatus," in the diaphragm through which the esophagus extends, becomes enlarged, allowing the stomach to pass through the hiatus into the thoracic cavity. GERD indicates a backflow of acid from the stomach into the esophagus. Although GERD may be an independent affliction, GERD is often a symptom of, or a co-affliction with, a hiatal hernia. Representative surgical treatments for GERD and/or hiatal hernia may include one or more of the following: a fundoplication, more specifically an open or laparoscopic Nissen fundoplication, where part of the fundus of the stomach is wrapped around the lower end of the esophagus to recreate or augment the lower esophageal sphincter (LES); a cruroplasty, which involves tightening the crura of the diaphragm around the esophagus; and an endoscopic gastroplication where pleats are formed within the esophagus at or near the LES, reducing the size of the internal diameter of the lower esophagus.

It has been known to use a prosthetic repair fabric in the surgical treatment of GERD and/or hiatal hernia. Typically, a sheet of surgical mesh fabric, such as BARD MESH, commercially available in rectangular stock sheets, is custom fashioned by a surgeon into a shape suitable for a particular patient's hiatal repair, such as a rectangular or oval shape. The surgeon forms a keyhole opening in the patch by cutting a slit from one edge of the implant and then forming an opening at the end of the slit that is large enough to receive the esophagus. The adjacent flaps of mesh formed by the slit running through the edge, known as "tails" or "fins", may be stitched together after the esophagus has been positioned in the keyhole opening, recreating a hiatal ring about the esophagus to help prevent the stomach from reentering the thoracic cavity.

It is one object of certain embodiments of the present invention to provide a preformed prosthesis for the treatment of GERD and/or the repair of hiatal hernias.

It is another object of certain embodiments of the present invention to provide a prosthesis for the treatment of GERD and/or the repair of hiatal hernias that reduces the incidence of postoperative adhesions to the esophagus, stomach and/or other surrounding viscera.

It is a further object of certain embodiments of the present invention to provide methods of treating GERD and/or repairing hiatal hernias.

SUMMARY OF THE INVENTION

In one embodiment of the invention, an implantable prosthesis is provided for repairing a tissue or muscle wall defect located near the esophagus. The implantable prosthesis comprises a layer of repair fabric that is susceptible to the formation of adhesions with tissue and organs, a surface barrier that inhibits the formation of adhesions with tissue and organs, and at least one edge barrier that inhibits the formation of adhesions with tissue and organs. The layer of repair fabric includes first and second surfaces and at least one fabric edge extending from the first surface to the second surface. The first surface is adapted to face the tissue or muscle wall defect when the implantable prosthesis is placed in a patient near the esophagus, and the second surface is adapted to face away from the tissue or muscle wall defect and toward the patient's cavity viscera. The layer of repair fabric has an opening that is adapted to receive the esophagus. The surface barrier is disposed on at least a portion of the second surface of the layer of repair fabric to inhibit the formation of adhesions between the portion of the second surface and adjacent tissue and organs when the implantable prosthesis is placed in the patient. The at least one edge barrier extends about at least a portion of the at least one fabric edge to inhibit the formation of adhesions between the portion of the at least one fabric edge and adjacent tissue and organs.

In another embodiment of the invention, an implantable prosthesis is provided for repairing a tissue or muscle wall defect located near a tube-like structure. The implantable prosthesis comprises a body portion that is constructed and arranged to be placed proximate the tissue or muscle wall defect, and includes an outer periphery and has an opening that is adapted to receive the tube-like structure. The body portion comprises a layer of repair fabric that is susceptible to the formation of adhesions with tissue and organs, and a surface barrier that inhibits the formation of adhesions. The layer of repair fabric includes first and second surfaces and at least one fabric edge extending from the first surface to the second surface. The first surface is adapted to face the tissue or muscle wall defect when the implantable prosthesis is placed in a patient near the tube-like structure. The layer of repair fabric has a first slit extending from the opening to the outer periphery to receive the tube-like structure in the opening. The surface barrier is disposed at the second surface of the layer of repair fabric to inhibit the formation of adhesions on the second surface when the implantable prosthesis is placed in the patient. The surface barrier has a second slit extending from the opening to the outer periphery to receive the tube-like structure in the opening. The second slit is offset from the first slit, such that the second slit overlies a portion of the layer of repair fabric and the first slit overlies a portion of the surface barrier.

In yet another embodiment of the invention, an implantable prosthesis is provided for repairing a tissue or muscle wall defect located near a tube-like structure. The implantable prosthesis comprises a body portion that is constructed and arranged to be placed proximate the tissue or muscle wall defect, and includes an outer periphery and has an opening that is adapted to receive the tube-like structure. The body portion comprises a layer of repair fabric that is susceptible to the formation of adhesions with tissue and organs, and a plurality of barriers that inhibit the formation of adhesions on selected portions of the layer of repair fabric when the implantable prosthesis is placed in the patient. The layer of repair fabric includes first and second surfaces, an outer peripheral edge and an opening edge. The first surface is adapted to face the tissue or muscle wall defect when the implantable prosthesis is placed in a patient near the tube-like structure. The outer peripheral edge extends from the first surface to the second surface along the outer periphery, and the opening edge extends from the first surface to the second surface along the opening. The plurality of barriers includes a surface barrier that is disposed on at least a portion of the second surface of the layer of repair fabric, a peripheral edge barrier that is disposed along at least a portion of the outer peripheral edge of the layer of repair fabric, and an opening edge barrier that is disposed along at least a portion of the opening edge of the layer of repair fabric.

In a further embodiment of the invention, an implantable prosthesis is provided for repairing a tissue or muscle wall defect located near a tube-like structure. The implantable prosthesis comprises a prosthetic repair fabric that includes an outer periphery and has an opening therein that is adapted to receive the tube-like structure. The prosthetic repair fabric includes first and second segments, each of the first and second segments including a layer of fabric that is susceptible to the formation of adhesions with tissue and organs. Each of the first and second segments includes a first end and a second end, the first end of the first segment overlapping the first end of the second segment at a first overlap area, the second end of the first segment overlapping the second end of the second segment at a second overlap area. The first segment includes a first mid-portion between the first and second overlap areas and the second segment includes a second mid-portion between the first and second overlap areas. Each of the first and second mid-portions forms a portion of the outer periphery of the prosthetic repair fabric that is equal to or greater than approximately 90 degrees.

In another embodiment of the invention, an implantable prosthesis is provided for repairing a tissue or muscle wall defect located near a tube-like structure. The implantable prosthesis comprises a prosthetic repair fabric having an opening that is adapted to receive the tube-like structure, and includes first and second segments. Each of the first and second segments includes a layer of repair fabric that is susceptible to the formation of adhesions with tissue and organs and a surface barrier that inhibits the formation of adhesions with tissue and organs. The surface barrier is disposed on a surface of the layer of repair fabric. Each of the first and second segments includes a first end and a second end, the first end of the first segment overlapping the first end of the second segment at a first overlap area. The first overlap area is free of one of the layer of fabric and the surface barrier of at least one of the first and second segments.

In a further embodiment of the invention, a prosthetic repair fabric comprises a body portion of implantable, biocompatible prosthetic material. The body portion includes a middle section having a first width and a pair of end portions extending in a longitudinal direction from opposite sides of the middle section. Each end portion has a second width that is greater than the first width.

In yet another embodiment of the invention, a method is provided for treating gastroesophageal reflux disease. The method comprises creating at least one external fold on the external wall of the esophagus; and cinching the at least one external fold to create at least one external plication on the esophagus.

Other objects and features of the present invention will become apparent from the following detailed description when taken in connection with the accompanying drawings. It is to be understood that the drawings are designed for the purpose of illustration only and are not intended as a definition of the limits of the invention.

BRIEF DESCRIPTION OF THE DRAWINGS

The foregoing and other objects and advantages of the invention will be appreciated more fully from the following drawings, wherein like reference characters designate like features, in which.

DESCRIPTION OF ILLUSTRATIVE EMBODIMENTS

Figure 1:
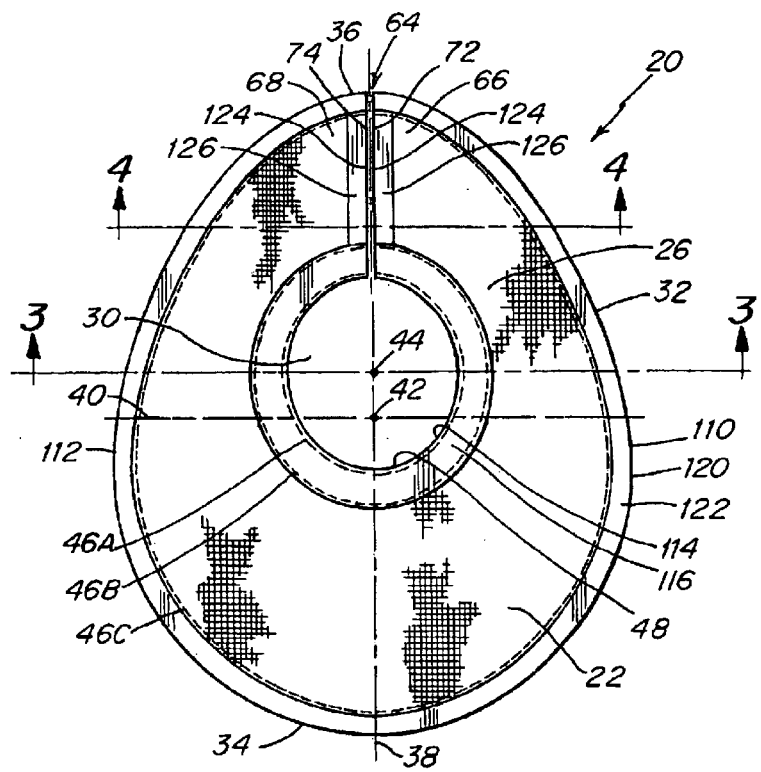
FIG. 1 is a top plan view of a prosthetic repair fabric in accordance with one illustrative embodiment of the present invention.

The invention is directed to an implantable prosthesis for repairing or augmenting anatomical weaknesses or defects, and is particularly suitable for the repair of soft tissue and muscle wall openings. For ease of understanding, and without limiting the scope of the invention, the prosthesis to which this patent is addressed is described below particularly in connection with a hiatal hernia repair and/or treatment of GERD. It should be understood, however, that the prosthesis is not so limited and may be employed in other anatomical procedures, as would be apparent to one of skill in the art. For example, the prosthesis may be used where a tube-like structure, or other projection, passes through an opening in a tissue, muscle or organ wall, or projects from a tissue, muscle or organ wall, requiring repair and/or augmentation.

Furthermore, while many of the embodiments discussed below include an implant having one or more portions that are tissue infiltratable, the invention is not so limited and also contemplates a prosthesis that is not arranged for tissue ingrowth. Still further embodiments include implants where tissue infiltratable or otherwise adhesion sensitive portions are rendered resistant to adhesion formation. In certain embodiments, some or all portions of the implant may be arranged for tissue ingrowth, while in other embodiments some or all portions of the implant may be arranged to resist tissue ingrowth or otherwise to resist the formation of adhesions to and strangulation of neighboring viscera. The location of tissue ingrowth sections and barrier sections may vary along an edge of the implant, a surface of the implant, and/or sections of a body portion of the implant, as discussed below.

An implant according to the present invention, in connection with a hiatal repair, may include a body portion constructed and arranged to cover the enlarged or weakened portion of the hiatus, or the operative sutures used in repairing the hernia, such as are placed in a cruroplasty. Some or all of the body portion may be tissue infiltratable, may be impervious to tissue ingrowth or otherwise resistant to the formation of adhesions, or may include a combination of tissue infiltratable and adhesion resistant regions. In some embodiments, the prosthesis may be arranged to reduce the incidence of the formation of post-operative adhesions or strangulation of the cord structure. The implant may be formed of a single or of multiple layers of prosthetic repair material, and the number of layers of prosthetic material may vary in different portions of the implant.

The implant may have a complete or partial opening that is adapted to receive the esophagus. The opening may be formed along any one, or a combination, of the sides of the implant or may be provided within and through the body portion. For the purposes of this patent specification, as well as any claims related thereto, the feature of an "opening" adapted to receive the esophagus or tube-like structure shall include a complete opening that is configured to completely surround the esophagus, and a partial opening that is configured to only partially surround the esophagus, even though the qualifier of "complete" or "partial" is not used. The opening may have a round shape or any other shape that is constructed and arranged to position the implant about the esophagus. A slit may also be formed extending from the opening to the periphery of the prosthesis to provide an access opening for the esophagus.

The implant may be defined by an anterior end, a posterior end, a medial side and a lateral side. The sides and ends may be of the same or of differing length and/or shape. Any of the sides and ends may include a single straight edge, a curved edge, an edge formed of diverging or converging segments, and other shapes as should be apparent to one of skill in the art. The implant, viewed end-to-end or side-to-side may be symmetrically shaped or asymmetrically shaped. The implant may have a circular shape, an ovoid or an egg shape, a C-shape, a bow tie shape, a butterfly shape, a rectangular shape, an arc shape, and other shapes as should be apparent to one of skill in the art.

The implant may be elongated in the anterior-posterior direction, in the medial-lateral direction or in a combination of the anterior-posterior and medial-lateral directions. An implant having substantially the same length in all directions also is contemplated. The implant may be preshaped or may be custom shaped by the surgeon prior to or during the surgical procedure. Similarly, the implant may be prearranged with the slit and keyhole opening, or one or both of these features may be left to the surgeon to form.

The implant may, in an unstressed or natural state, such as prior to implantation, have a generally flat or planar shape, or may be arranged with a concave and/or convex shape on one or more surfaces, or may include a more complex three dimensional shape. A cord or other member may be threaded through the implant and then manipulated, such as by drawing ends of the cord extending outside of the implant, to transform the prosthesis into a desired shape. The implant may be provided with shape influencing members, such as thin strips of metal, polymer, and the like, that may be engaged to, or otherwise in contact with, the implant and naturally or upon application of a force (e.g., heat) cause the prosthesis to form a predetermined shape.

The implant may be sufficiently flexible to allow a surgeon to manipulate the fabric to conform to the surgical site and ease delivery during a laparoscopic procedure, or may have a stiffer arrangement that limits compression and/or expansion of the repair device. In certain embodiments, the implant may be collapsible, such as by folding, rolling, or otherwise, into a slender configuration that may be delivered through a narrow lumen of a laparoscopic cannula or trocar. The flexibility of the implant is influenced by many factors including the materials from which the implant is constructed, any shape influencing members, treatments applied to the material of the implant, and the amount of stitching or other attachment features in the body of the implant.

Certain portions of the implant may include a barrier which may be formed, for example and without limiting the invention, by applying a barrier material to selective regions of the prosthesis, by rendering selected porous regions of the implant less porous and, preferably, impervious to tissue infiltration, and by other arrangements as should be apparent to one of skill in the art. The barrier may be arranged to isolate the esophagus, and/or the abdominal viscera, from selected portions of the implant that are tissue infiltratable, reducing the incidence of esophageal, stomach, liver, and intestine trauma associated with adhesion, constriction and the like.

As an example, and without limiting the inventive arrangements contemplated for isolating the esophagus and viscera from various potential points of adhesion to the implant, the opening edge may be arranged with an inner edge barrier so that the opening edge is isolated from the portion of the esophagus passing through the opening. Those margin areas surrounding the opening on the first, or diaphragm facing, surface of the implant also may be isolated by an edge barrier, limiting the prospects of contact between the segment of the esophagus extending through and adjacent the opening and the margins of the opening. Some or all of the second surface of the prosthesis, that is the surface which will face the viscera, may include a surface barrier. The surface barrier may be arranged to cover substantially the entire second surface. A further outer edge barrier may be arranged at the outer edge of the prosthesis to prevent adhesions with the cavity viscera by the outer periphery of the prosthesis. The outer edge barrier may also be configured or extended to isolate the margin of the first surface extending adjacent the outer edge of the layer of fabric. The keyhole slit may also have a slit barrier portion. The slit edges and/or the margin adjacent the slit edges of the tissue infiltratable fabric at the keyhole slit may also encompass a slit barrier. The shape and dimension of the various barrier portions may be modified as would be apparent to one of skill in the art, and the invention is not limited to the particular configuration of the barrier sections illustrated in the figures.

The implant may be formed from two or more segments that may be attached to each other at one or more overlap areas to form the prosthesis. Portions of the segments between the overlap areas may be configured to form approximately 90° or more of the outer periphery of the prosthesis. One or more of the overlap areas may have a nested configuration to maintain a generally uniform thickness across the prosthesis.

FIGS. 1–6 illustrate one embodiment of a prosthetic repair fabric for repairing soft tissue and muscle wall defects, particularly hiatal hernias, by promoting enhanced tissue ingrowth while limiting the incidence of postoperative adhesions to the repair fabric. The prosthesis 20 includes a body portion that is configured to cover the enlarged or weakened portion of the hiatus or the operative sutures repairing the hernia such as are applied in a cruroplasty. The body portion has a first surface 26 for facing the defect region, such as the diaphragm, and a second surface 28 for facing the viscera. The body portion includes a tissue infiltratable fabric 22. One or more regions of the body portion may be configured as adhesion resistant to limit the incidence of postoperative adhesions to selected regions of the prosthesis.

In certain repairs located proximate a tube-like structure, such as the esophagus, the prosthesis may be configured to accommodate or conform to the esophagus or other tube-like structure. In the illustrative embodiment, the prosthesis is provided with an opening 30 that is adapted to receive the esophagus. The opening 30 is located within the body portion of the prosthesis so that the esophagus is completely surrounded by the prosthesis when it is implanted at the defect site. It is to be appreciated that the opening may be provided on any suitable portion of the prosthesis for a particular repair. For example, the opening may be located along one or more sides of the prosthesis so as to only partially surround the esophagus with the prosthesis. The opening may have a round shape or any other shape that is adapted to conform to the esophagus.

A slit 64 extends from the opening to the outer periphery 32 of the prosthesis, providing a pathway for positioning the implant about the esophagus. The slit may be located on any portion of the prosthesis and oriented to extend between the opening and outer periphery from any suitable direction. The slit 64 and opening 30 may be pre-formed with the prosthesis or formed by a surgeon during the repair procedure.

As indicated above, one or more selected regions of the prosthesis 20 may be rendered adhesion resistant to limit the incidence of postoperative tissue adhesion between the prosthesis and adjacent tissue, muscle and/organs, such as the esophagus, spleen, liver, stomach, bowel, small and large intestine in the abdominal cavity or the heart and lungs in the thoracic cavity. In this regard, the prosthesis may include one or more barriers that are configured and arranged to isolate the tissue infiltratable fabric so as to inhibit undesirable adhesions. For example, the prosthesis may include any one or a combination of two or more of a surface barrier on one or both sides of the fabric, an edge barrier along one or more edges of the fabric and/or a margin barrier located proximate to one or more edges of the fabric. The shapes, sizes and locations of the various barriers may be selected to achieve any desired adhesion resistant characteristics for the prosthesis as would be apparent to one of skill in the art.

In the illustrative embodiment shown in FIGS. 1–6, the prosthesis includes a surface barrier 118 that is arranged to cover substantially the entire second surface 28 (viscera facing surface) of the fabric 22. In this manner, the surface barrier inhibits the formation of adhesions between the fabric and the cavity viscera located opposite the defect site. In one embodiment, the surface barrier 118 includes a sheet of adhesion resistant material that is attached to the fabric.

The prosthesis also includes an inner edge barrier 114 and an inner margin barrier 116 to isolate the esophagus from portions of the fabric 22 proximate the opening 30. More particularly, an opening edge 54, which extends between the first and second surfaces of the fabric and defines a fabric opening, is covered by the inner edge barrier 114 so that the portion of the esophagus passing through the opening does not directly contact the opening edge of the fabric. Similarly, a marginal portion 55 of the first surface 26 (diaphragm facing) surrounding the fabric opening is isolated by the inner margin barrier 116. The margin barrier limits the prospect of adhesions between the segment of the esophagus extending through and adjacent the opening and the marginal portions of the fabric proximate the opening.

In the illustrative embodiment, the inner margin barrier 116 includes an annular ring of barrier material that overlies the first surface 26 of the fabric 22 at the inner marginal portion 55 surrounding the opening 30. As shown, the inner edge 48 of the margin barrier extends slightly beyond the opening edge 54 of the fabric. Similarly, the inner edge of the surface barrier 118 extends inwardly beyond the opening edge of the fabric so as to lie adjacent the inner edge of the margin barrier. The inner edge of the margin barrier 116 is attached directly to the inner edge of the surface barrier 118, without the intervening layer of fabric therebetween, to form the inner edge barrier 114 and isolate the opening edge of the fabric from the esophagus.

The prosthesis further includes an outer edge barrier 120 that extends around at least a portion of the outer peripheral edge to reduce the incidence of adhesions between the cavity viscera and the outer periphery 32 of the prosthesis. In the illustrative embodiment, the outer edge barrier extends about the entire outer periphery of the prosthesis. The outer edge barrier 120 is formed by rendering a peripheral segment of the fabric 22 adhesion resistant. In one embodiment, the outer edge barrier is formed by melting and resolidifying or otherwise heat sealing the outer periphery of the fabric. It is to be understood, however, that the outer edge barrier may be formed by any suitable arrangement apparent to one of skill in the art. For example, a barrier material may be used to cover the fabric periphery or otherwise render the fabric adhesion resistant along the periphery. Examples of suitable outer edge barriers are described in U.S. application Ser. No. 09/661,623, assigned to C. R. Bard, which is incorporated herein by reference.

An outer margin barrier is provided to isolate a marginal portion of the fabric proximate the outer peripheral edge of the prosthesis. The outer margin barrier 122 extends inwardly from the outer edge along the first surface 26 of the fabric layer 22 to limit the likelihood of adhesion formation to the prosthesis were the outer edge 32 to fold back during placement or otherwise be exposed to tissue and organs post procedure. In one embodiment, the outer margin barrier is formed by melting and resolidifying the outer marginal portion of the fabric. However, any suitable isolation arrangement may be employed as would be apparent to one of skill, including the various barrier arrangements described above.

As indicated above, the prosthesis may be provided with a slit to allow ready access to the opening 30. In some instances, it may be desirable to isolate the slit edges and/or fabric margins along the entire length or a portion of the slit from the esophagus or other tube-like structure. In the illustrative embodiment of FIGS. 1–6, a slit edge barrier 124 is provided along each of the slit edges 72, 74 to isolate the slit from the esophagus as the prosthesis is placed about the esophagus. The slit edge barrier 124 may also reduce the incidence of adhesions between the slit and esophagus after implantation of the prosthesis. The prosthesis also includes a slit margin barrier 126 along the margin segments 65 adjacent each side of the slit 64 on the first side 26 of the fabric 22. In one embodiment, the slit edge barriers 124 and the slit margin barriers 126 are formed by melting or heat sealing the slit edges and margins of the fabric. It is to be understood, however, that any suitable isolation arrangement may be employed as would be apparent to one of skill, including the various barrier arrangements described above.

Figure 2:
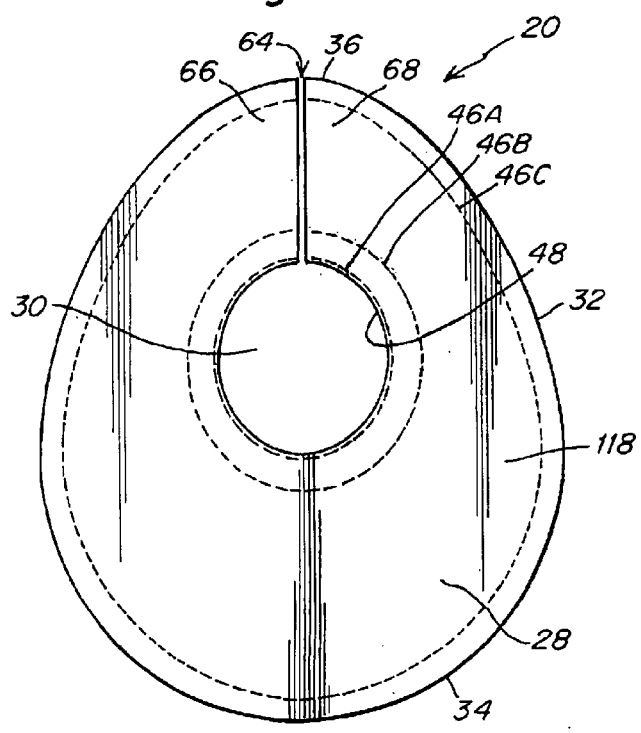
FIG. 2 is a bottom plan view of the prosthetic repair fabric of FIG. 1.
Figure 3:
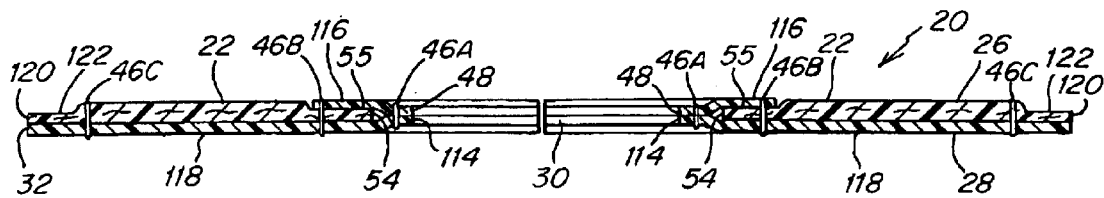
FIG. 3 is a cross-sectional view of the prosthetic repair fabric of FIG. 1 taken along section line 3—3.
Figure 4:
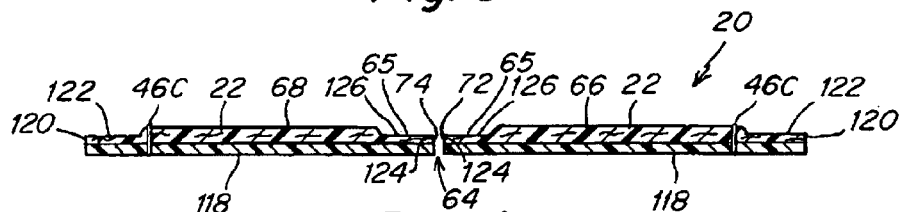
FIG. 4 is a cross-sectional view of the prosthetic repair fabric of FIG. 1 taken along section line 4—4.
Figure 5:
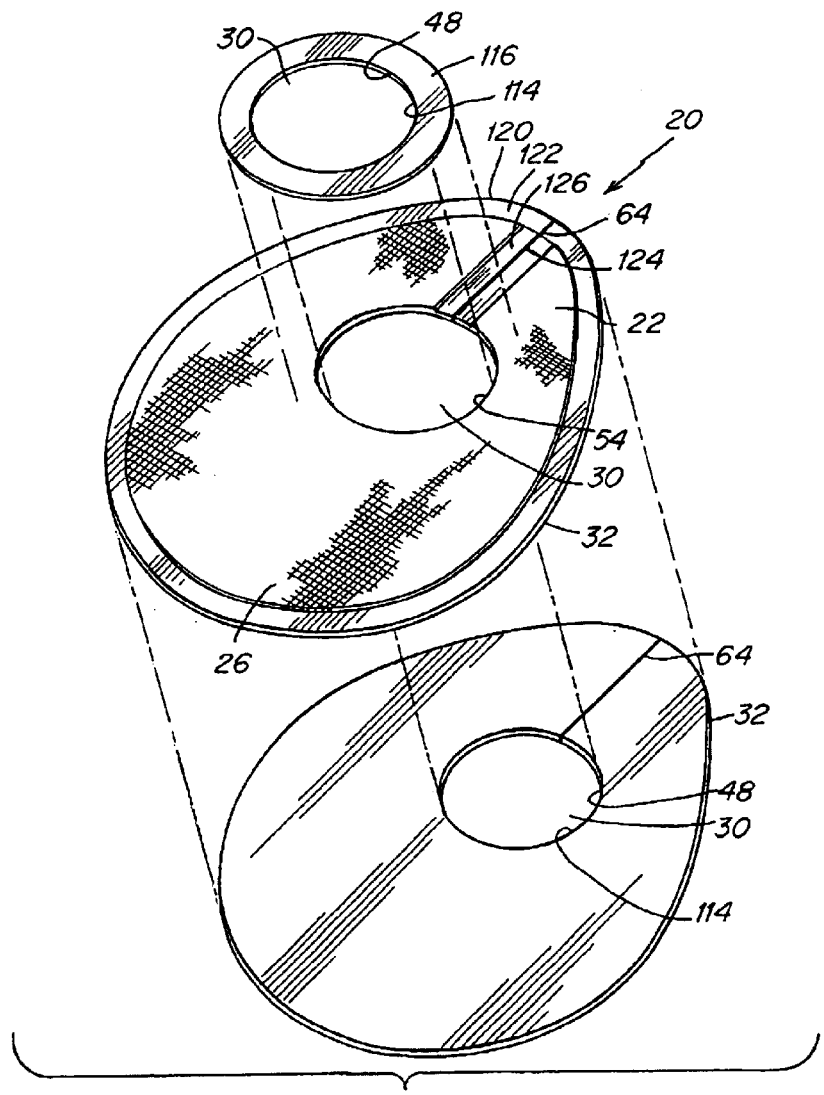
FIG. 5 is an exploded top perspective view of the prosthetic repair fabric of FIG. 1.
Figure 6:
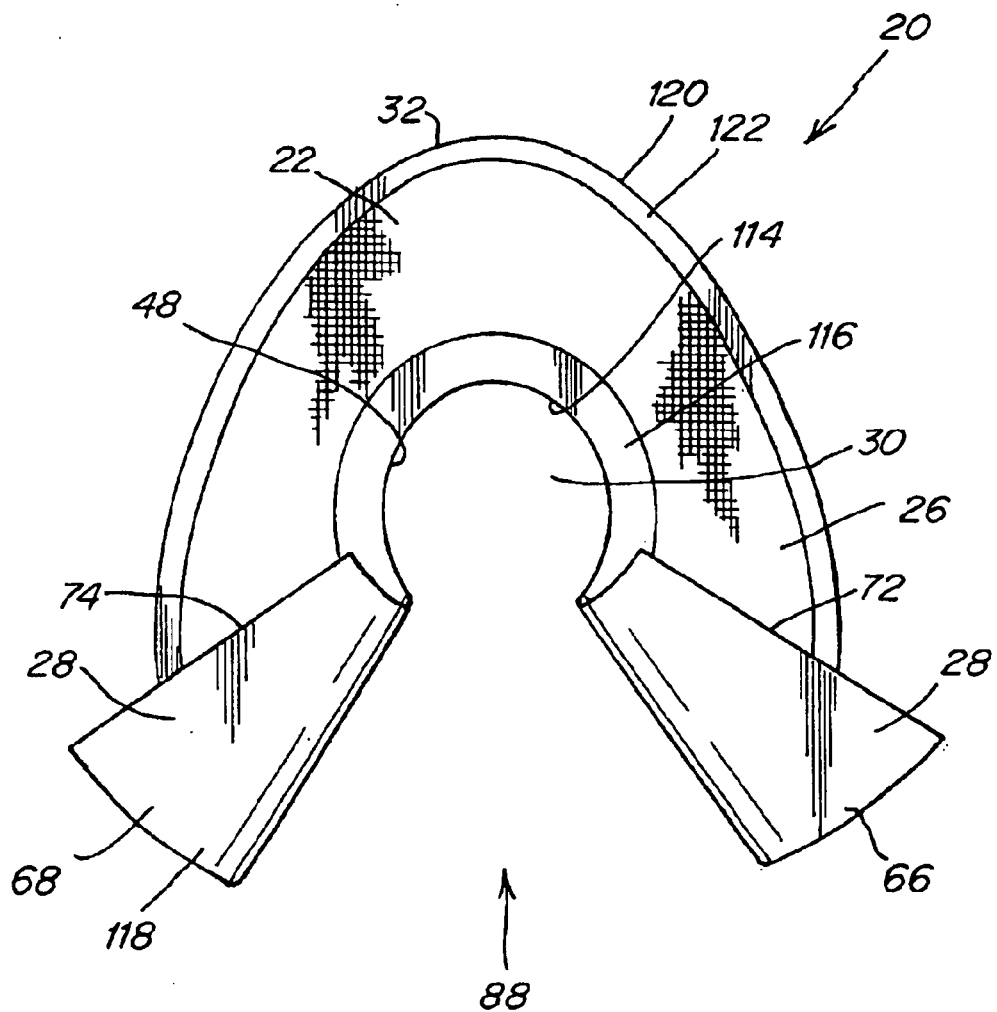
FIG. 6 is a top view of the prosthetic repair fabric of FIG. 1 with the slit and opening exposed to receive the esophagus.

In the illustrative embodiment shown in FIGS. 1–6, the inner edge barrier 114, the inner margin barrier 116 and the surface barrier 118 are stitched to the fabric 22 with a series of continuous connecting stitches 46. As shown in FIGS. 1–2, a pair of stitch lines 46A, 46B attach the annular barrier material to the fabric 22 and the surface barrier 118 to form the inner edge barrier 114 and the inner margin barrier 116. The first line of stitches 46A attaches the inner peripheries of the annular barrier material and the surface barrier 118 directly to each other to form the inner edge barrier 114 which substantially isolates the inner edge 54 of the fabric 22 from the esophagus. The second line of stitches 46B attaches the outer circumference of the inner margin barrier 116 and corresponding region of the surface barrier 118 to the fabric 22. A third line of stitches 46C attaches the outer circumference of the surface barrier 118 to the fabric along the outer periphery 32 of the implant.

It may be desirable to provide the surface barrier 118 with some amount of slack so that the barrier does not necessarily lie directly against the second surface of the fabric 22. In this manner, the surface barrier is not tautly drawn against the surface of the fabric, thereby allowing slight billowing of the barrier, which may enhance tissue integration of the prosthesis. In one embodiment, the portion of the surface barrier 118 extending between the second and third stitch lines 46B, 46C is configured to billow slightly relative to the fabric.

It is to be understood that other suitable stitch patterns may be implemented for connecting one or more of the barriers to the fabric 22. Examples of other stitch patterns include, but are not limited to, a plurality of intermittent stitches between the barrier and the fabric, or a single line of continuous stitches that follow the contour of the periphery 32 and form a concentric, spiral pattern from the outer periphery 32 to the inner edge 48 of the prosthesis 20. It may be desirable to limit the amount of stitching to maintain the flexibility of the prosthesis. Appropriate biocompatible thread materials may be used for joining the barrier and tissue infiltratable materials together, as would be apparent to one of skill in the art. For example, the stitches may include, but are not limited to, polypropylene monofilament or ePTFE yarn.

Rather than stitching the barrier materials to the fabric, other attachment methods may be employed as would be apparent to one of skill in the art. For example, the barrier and the fabric may be attached using any suitable tacking, stapling, heat bonding, chemical bonding and molding techniques.

While specific barrier structures have been described above in connection with various portions of the prosthesis, it is to be appreciated that other suitable barrier structures may be employed with the prosthesis as would be apparent to one of skill in the art. For example, any one or combination of barriers may be formed by altering or treating the fabric so as to occlude tissue ingrowth, by covering the fabric with a barrier material, or any combination of fabric treatment and barrier materials. Additionally, any one or more of the barrier structures may be formed by both treating the fabric layer and covering the treated fabric with a barrier layer. Several additional embodiments of other barrier arrangements are described below.

Figure 7:
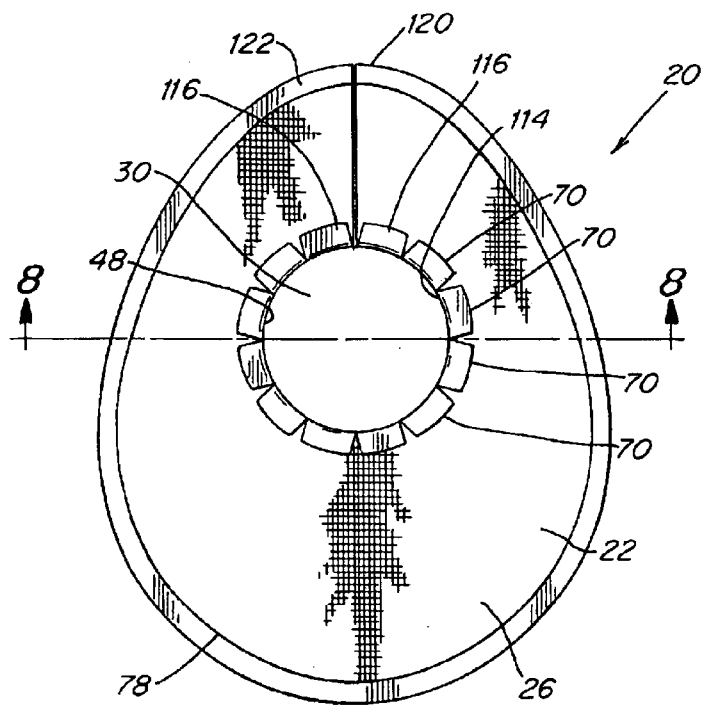
FIG. 7 is a top plan view of a prosthetic repair fabric in accordance with a further illustrative embodiment of the present invention.
Figure 8:
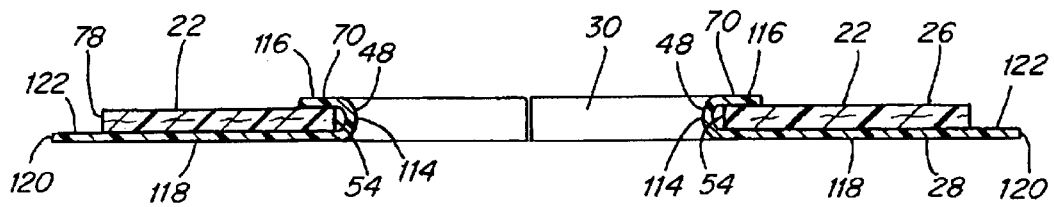
FIG. 8 is a cross-sectional view of the prosthetic repair fabric of FIG. 7 along section line 8—8.

FIGS. 7–8 illustrate another embodiment for the inner edge barrier to reduce the incidence of adhesions to the esophagus. As shown in FIG. 8, the inner edge barrier 114 extends from the surface barrier 118 on the second surface of the tissue infiltratable fabric 22 and across the inner edge of the fabric opening. The barrier material wraps about the opening edge 54 and onto the first surface of the fabric 22 to form the inner margin barrier 116. If the inner margin barrier is unnecessary or not desired, the barrier material may be configured to extend from the surface barrier 118 and across only the opening edge of the fabric. The inner edge barrier 114 and/or inner margin barrier 116 may be joined to the fabric using any suitable attachment arrangement such as by bonding, stitching, fusing and the like. Wrapping the barrier material about the opening edge of the fabric layer provides the surface barrier 118, the inner barrier 114, and the inner barrier 116 as a continuous, integrated structure. In this arrangement, the inner edge barrier 114 is integrally attached to the surface of barrier 118, as a contiguous, integral material.

To facilitate fabrication of the inner edge barrier 114 and/or the inner margin barrier 116, the surface barrier 118 may include a plurality of flaps 70 that are configured to fold into and extend through the opening in the tissue infiltratable fabric. The flaps 70 may be wrapped about and joined to the fabric or may remain unsecured; in either arrangement, the flaps of barrier material are to be positioned between the esophagus and the tissue infiltratable layer, thereby reducing the incidence of adhesions with the fabric edge of the opening or other potential damage to the esophagus. The flaps 70 may be attached to the fabric using any suitable arrangement, such as by stitching, adhesive bonding, chemical bonding, and the like. The flaps may be wrapped about and attached to the fabric before or during the procedure or may be provided integrally formed to the tissue infiltratable layer. Those skilled in the art will also recognize that the barrier flaps may be separately attached to the tissue infiltratable fabric, rather than extend from the barrier 118. The flaps may also extend through the opening and extend away from the viscera facing side of the implant.

Figure 9:
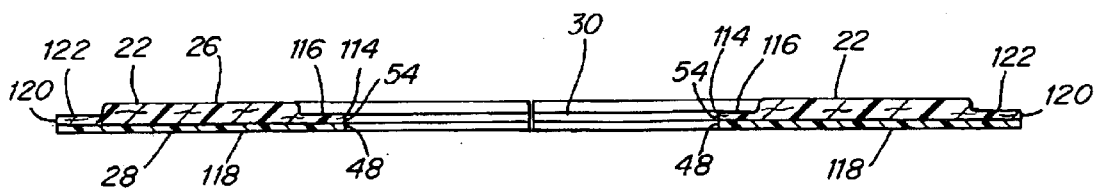
FIG. 9 is a cross-sectional view similar to FIG. 8 of a prosthetic repair fabric in accordance with another illustrative embodiment of the present invention.

Rather than forming the inner edge barrier 114 and the inner margin barrier 116 from a layer of barrier material that covers portions of the fabric, it may be desirable to treat or alter selected portions of the fabric to render those portions of the fabric resistant to adhesion formation with tissue and organs. In another illustrative embodiment shown in FIG. 9, the inner edge 54 of the fabric 22 is melted and resolidified to form the inner edge barrier 114 and/or the inner margin barrier 116 about the inner edge and/or inner margin of the fabric, respectively. If desired, those portions of the fabric may also be covered with separate barrier material to further enhance the adhesion resistant characteristics of the barriers 114, 116.

In some instances, it may be desirable to form the outer edge barrier 120 and outer margin barrier 122 from barrier material that is arranged to cover selected portions of the fabric 22. In the illustrative embodiment shown in FIG. 7, the outer edge barrier 120 and the outer margin barrier 122 extend from the surface barrier 118 covering the viscera facing side. As shown, the surface barrier is configured to extend beyond the outer edge 78 of the tissue infiltratable layer 22 to isolate the outer edge and/or outer margin of the fabric from contact with organs and tissue. It is to be appreciated that this extension of the surface barrier may be folded about the outer edge and over a portion of the first surface of the tissue infiltratable layer and joined to the fabric by stitching, chemical bonding, heat bonding and the like.

The prosthesis 20 may be provided with one or more barriers that are pre-attached to the fabric and/or other barriers. Alternatively, the prosthesis may be provided as a kit of separate parts with the barriers either being attached to the fabric and/or other barriers during the repair procedure or simply overlaid on a desired portion of the fabric 22 to be held in place by adjacent tissue and/or organs.

In one embodiment, the tissue infiltratable layer 22 is formed of a sheet of biologically compatible, flexible, prosthetic repair fabric having a plurality of interstices or openings which allow tissue ingrowth, integrating the repair device to host tissue after implantation. The suture pull-out strength of the tissue infiltratable layer and/or the barrier portions should be sufficient to support the underlying anatomical weakness and withstand the dynamic environment of the implant area. In the case of hiatal hernia repair, the mesh preferably has a suture pull-out strength of approximately 2 pounds per square inch and is sufficiently flexible to accommodate the dynamic environment about the esophagus during respiration, coughing, and swallowing. A representative material is knitted polypropylene monofilament mesh, such as BARD MESH, available from C. R. Bard, Inc. When implanted, the polypropylene mesh promotes rapid tissue ingrowth into and around the mesh structure. Alternatively, other surgical materials which are suitable for tissue reinforcement in defect closure may be utilized including, without limitation, polytetrafluoroethylene (PTFE) mesh, PROLENE, SOFT TISSUE PATCH (microporous ePTFE), SURGIPRO, TRELEX, ATRIUM, MERSELENE, non-absorbable collagen, and polyester. Absorbable materials, including polyglactin (VICRYL), polyglycolic acid (DEXON), and absorbable collagen may also be employed. It is contemplated that the fabric may be formed from monofilament or multifilament yarns which may be woven, knitted, molded, or otherwise interengaged to form the tissue infiltratable component of the implant.

In one embodiment, one or more of the barriers may be formed from a sheet of expanded polytetrafluoroethylene (ePTFE), such as GORE-TEX available from W. L. Gore & Associates, Inc., having a pore size (submicronal) that discourages tissue ingrowth and adhesion. A representative and non-limiting sampling of other suitable barrier materials includes silicone elastomer, such as SILASTIC Rx Medical Grade Sheeting (Platinum Cured) distributed by Dow Corning Corporation, TEFLON mesh, microporous polyproplyene sheeting (CELGARD), collagen, hyaluronic acid, carboxymethyl cellulose, and glycolic acid polymers. Autogenous, heterogeneous, and xenogeneic tissue also are contemplated including, for example, pericardium and small intestine submucosa. Absorbable materials, such as oxidized, regenerated cellulose (INTERCEED (TC7)) may be employed for some applications. The barrier can be a blend, mixture, or hydrogel of any of the materials to form a temporary or permanent barrier for adhesion formation.

As indicated above, one or more of the barriers may be formed by treating or altering a portion of the tissue infiltratable layer to form a surface that does not promote tissue ingrowth. In one embodiment, one or more portions of the fabric layer are melted and resolidifed to render those portions of the fabric adhesion resistant. Other suitable techniques may include ultrasonic, induction, vibration, infrared/laser welding and the like. The fabric pores may be sealed with compatible materials to prohibit tissue ingrowth. As is to be appreciated, any suitable method may be used to render selected portions of the prosthesis adhesion resistant as would be apparent to one of skill in the art.

The prosthesis 20 of tissue infiltratable fabric and barrier regions is relatively flat and sufficiently pliable to allow a surgeon to manipulate the shape of the implant to conform to the anatomical site of interest and to be sutured or stapled thereto. The prosthesis 20 may be delivered, if desired, to the patient's cavity through a trocar or a laparoscopic cannula for skin incision. The shape and size of the prosthesis 20, including the fabric 22 and any of the barriers, may vary according to the surgical application as would be apparent to one of skill in the art. In this regard, it is contemplated that the fabric and/or any barrier may be pre-shaped or shaped by the surgeon during the surgical procedure.

In some instances, it may be desirable to pre-shape the prosthesis 20 to fit the general anatomy near a hiatal hernia. The prosthesis 20 may be shaped to fit within the abdominal cavity and positioned under the diaphragm and around the esophagus or under the diaphragm and proximate the esophagus. Alternatively, the prosthesis may be shaped to fit within the thoracic cavity and positioned over the diaphragm, over any hiatus, and/or over any suture site for a cruroplasty or fundoplication.

In the illustrative embodiment shown in FIGS. 1–6, the prosthesis has a generally oval or egg shape suitable for augmenting or repairing a hiatal or other diaphragmatic hernia. The geometry of the prosthesis 20 is substantially elliptical with a major axis 38 and a minor axis 40 that intersect at an origin 42 located at the mid-point of both axes. As illustrated in FIG. 1, the prosthesis is substantially symmetric about the major axis 38 and is substantially asymmetric about the minor axis 40, providing a generally ellipsoid shape (e.g., egg shape) with a narrower or acute end 36, a wider or obtuse end 34, and lateral and medial sides 110, 112 that converge towards each other in a direction from the obtuse end toward the acute end. It is to be appreciated that the prosthesis may be configured with any suitable shape, such as a shape that is symmetric about both axes, asymmetric about both axes, or asymmetric about the major axis and symmetric about the minor axis.

The opening 30 for receiving the esophagus or other tube-like structure may be positioned in any desirable location, relative to the body portion, that is suitable for a particular repair. In the illustrative embodiment, the opening 30 is positioned with its center 44 located along the major axis 38 and off-set from the minor axis 40 of the body toward the acute end 36. As shown, the opening has a circular or ovoid shape configured to receive the esophagus or other tube-like structure, although any suitably shaped opening apparent to one of skill in the art may be employed with the prosthesis.

In the illustrative embodiment shown in FIGS. 1–6, the prosthesis includes a pair of tails 66, 68 at the acute end 36 of the body portion. The tails 66, 68, which are separated by the slit 64, independently or together may be spread, lifted, folded back or otherwise separated to create an access passage 88 for introducing the esophagus to the opening 30. In an unstressed, natural configuration of the implant, the tails lie adjacent each other on opposite sides of the slit in a substantially planar arrangement, as shown in FIG. 1.

In one exemplary embodiment associated with FIGS. 1–6, the prosthesis 20 includes an approximately 0.025 to 0.030 inch thick sheet of BARD MESH knitted from polypropylene monofilament with a diameter of approximately 0.006 inches. The surface barrier 118, and the inner margin barrier are formed with approximately 0.006 to 0.008 inch thick sheets of ePTFE attached to the mesh and each other using approximately 4 mm to 6 mm long stitches formed of a 0.006 inch diameter polypropylene monofilament. The prosthesis 20 has a length along the major axis 38 of approximately 10.5 cm and a width along the minor axis 40 of approximately 8.4 cm.

The opening 30 in the prosthesis 20 is substantially circular and sized to accommodate an esophagus. A small esophagus is typically 2–3 cm in diameter and a large esophagus is typically 3–4 cm in diameter. It may be desirable to size the opening so as to allow approximately 0.25 cm spacing between the opening edge 48 of the prosthesis 20 and the esophagus. In one embodiment, the opening has a diameter of approximately 2.5 centimeters to approximately 4.5 centimeters. For accommodating a small esophagus, the opening may be configured with a diameter of approximately 2.5 to approximately 3.5 centimeters, and preferably approximately 3 centimeters. For accommodating a large esophagus, the opening may be configured with a diameter of approximately 3.5 centimeters to approximately 4.5 centimeters, and preferably approximately 4 centimeters. It is to be understood, however, that the opening may be configured to have any shape and size suitable for receiving an esophagus or other tube-like structure.

In the embodiment shown in FIG. 1, the opening 30 is aligned with the major axis 38 and offset by approximately 0.8 cm from the minor axis 40 towards the acute end 36 of the prosthesis 20. The opening in the mesh fabric 22 has a radius of approximately 1.9 cm. The annular shaped barrier layer 116 overlays the mesh fabric 22 proximate the fabric opening and has an inner radius of approximately 1.4 cm and an outer radius of approximately 2.4 cm; thus, the annular barrier has a width of approximately 1.0 cm of which approximately 0.5 cm overlays the first surface of the mesh fabric 22 and approximately 0.5 cm extends beyond the inner edge 54 of the mesh fabric 22.

The surface barrier 118 is substantially symmetric with the mesh fabric 22 along the outer periphery 32, and the opening in the surface barrier 118 is symmetric to the inner radius of the annular barrier 116, which in the embodiment shown in FIG. 1 is 1.4 cm. The inner edges 48 of the annular barrier layer and the surface barrier extend approximately 0.5 cm beyond the inner edge 54 of the opening 30 in the mesh fabric 22. Thus, in the embodiment shown in FIG. 1, the opening 30 defined by inner edges 48 of the barriers has a diameter of approximately 2.8 cm.

The outer edge and margin barriers 120, 122 are situated along the outer edge and margin of the outer periphery 32 of the mesh fabric 22 and formed by heat melding the mesh fabric 22 to close the interstices or openings in the mesh fabric 22 and to seal the mesh to the barrier 118. The outer margin barrier 122 has a width of approximately 1/16 to 3/8 inch. The slit edges and margins of the mesh fabric at the slit 64 are also heat sealed to form slit barriers 124, 126.

It should be understood that the dimensions provided above are merely exemplary and that any suitable sizes and shapes may be employed for the prosthesis 20.

Figure 10:
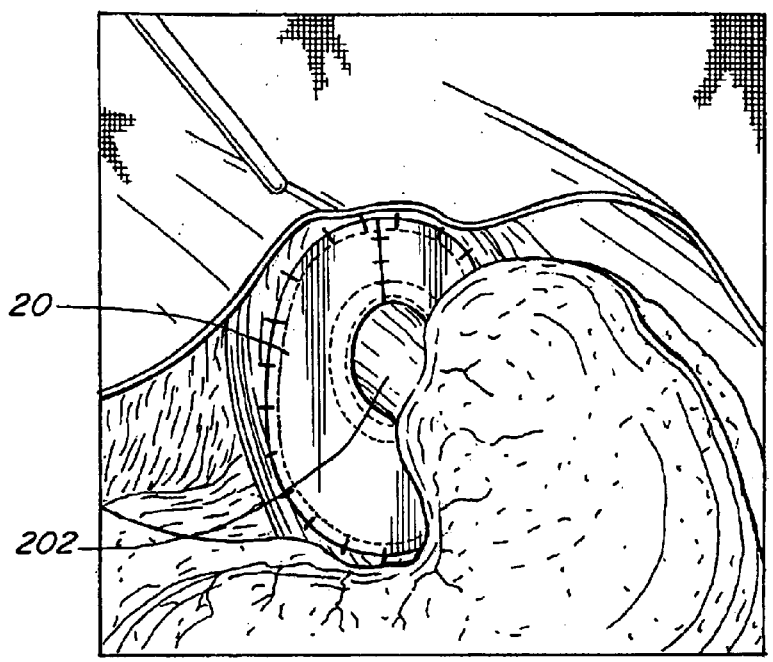
FIG. 10 is a schematic view illustrating the prosthetic repair fabric of FIG. 1 implanted in the abdominal cavity proximate to the esophagus.
Figure 11:
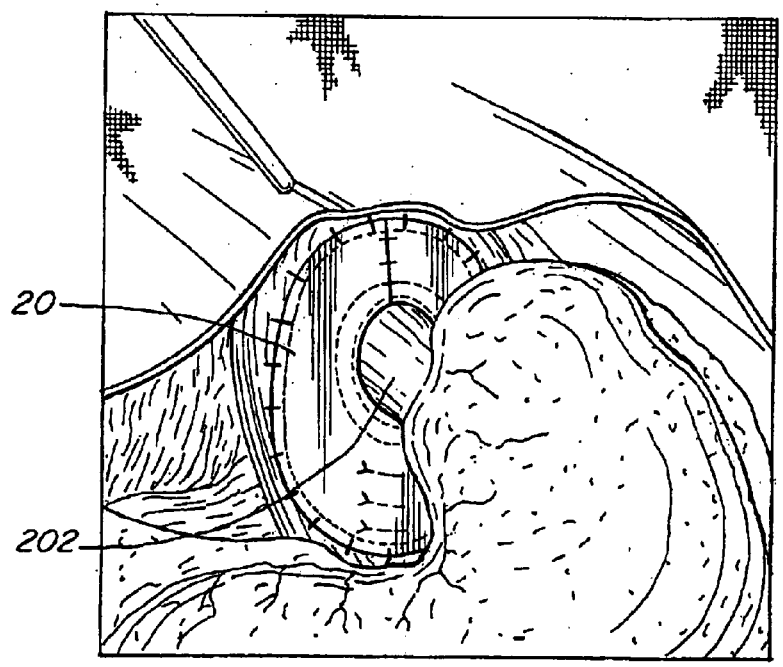
FIG. 11 is a schematic view illustrating the prosthetic repair fabric of FIG. 1 implanted in the abdominal cavity proximate to the esophagus following a cruroplasty procedure.

FIGS. 10–11 illustrate several representative applications of the prosthesis in the repair of a hiatal hernia and/or in the treatment of GERD. As shown in FIG. 10 the prosthesis 20 may be placed over the defect without approximating the tissue, effecting the repair in a substantially tension-free manner. As shown in FIG. 11, the prosthesis may be employed in conjunction with a cruroplasty to reinforce the stitches with tissue infiltration over a surface area and alleviate the likelihood of suture pullout when a force is applied to the crura, that otherwise potentially could lead to recurrent herniation. It is to be understood that the prosthesis may be employed in any suitable manner for other procedures as would be apparent to one of skill.

After placement of the prosthesis at the defect site, with the esophagus extending through the opening 30 and with the first surface 26 facing the diaphragm, the prosthesis 20 may be rotated such that the acute end of the prosthesis is positioned toward the posterior of the patient, where it may be easier to suture or otherwise join the tails together. It is known, for example, during a cruroplasty to bias the esophagus superiorly and anteriorly to facilitate the suturing behind and below the esophagus. After the tails have been attached to each other to close off the access opening, the implant may be rotated or otherwise manipulated so that the acute end 36 with the tails is positioned anteriorly and the obtuse end 34 is located posteriorly over the hiatal defect. Since the obtuse end may have greater structural integrity than the acute end, which includes the tails sections held together by operatively placed sutures, it may be desirable then to position the obtuse end of the prosthesis over the defect site.

In some instances, it may be desirable to overlap and secure the tails 66, 68 to each other. Overlapping the tails may enhance the structural integrity of the prosthesis along the access passage to the opening. Tail overlap may also facilitate adjustment of the prosthesis about the esophagus or other structure. It may also allow a surgeon to create a desirable non-planar or three-dimensional shape for the prosthesis that conforms to the defect site.

Figure 12:
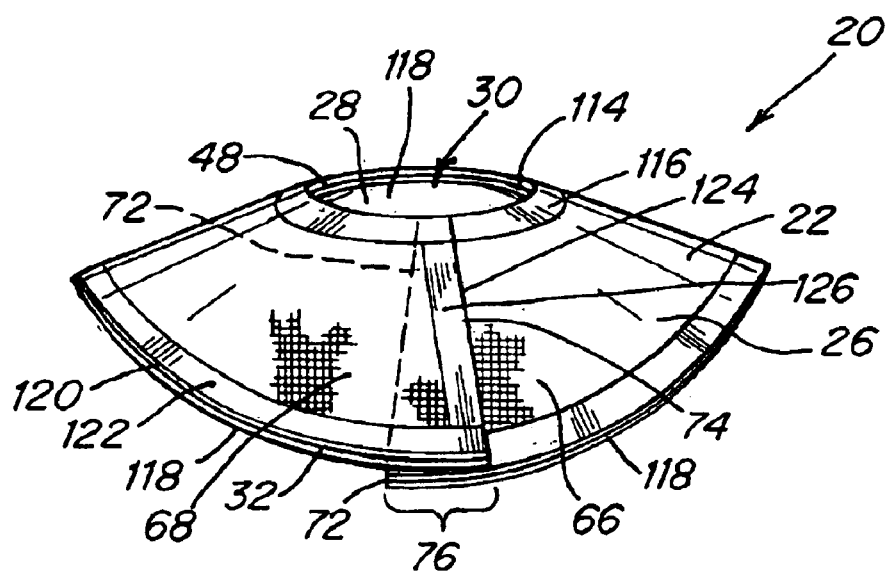
FIG. 12 is a side elevational view of the prosthetic repair fabric of FIG. 1 with overlapped tails.

In the illustrative embodiment shown in FIG. 12, the tails 66, 68 are overlapped so that the implant acquires a generally conical shape with a generally concave surface facing the viscera and a generally convex surface facing the diaphragm, specifically the crura. Providing a convex shaped diaphragm facing surface may facilitate seating of the implant to the slightly concave and irregular surface of the diaphragm. The implant may be arranged to include one of the concave/convex surfaces, both concave/convex surfaces, or neither of the concave/convex surfaces, as would be apparent to one of skill in the art. Further, the concavity/convexity shapes may be reversed; that is, the diaphragm facing surface may include a concave shape and/or the viscera facing surface may include a convex shape. Rather than manipulating the prosthesis into a particular shape, it is to be appreciated that the implant may be preformed to have any desired shape, such as a convex and/or concave appearance.

It may be desirable to configure the prosthesis with tails that overlap each other when the implant is in a natural unstressed state. In this manner, the tails may be joined together without changing the shape and/or inducing tension in the prosthesis. That is, the shape of the implant may remain essentially unchanged after the tails are sutured or otherwise attached together, forming a strong, complete ring around the esophagus without imparting tension to the prosthesis.

In one illustrative embodiment shown in FIGS. 13–16, the prosthesis 20 is configured with the tails 66, 68 overlapped at an overlap region 76 when the implant lies substantially flat. If desired, the tails can be drawn further together, inducing tension in the implant which may cause the prosthesis 20 to assume a non-planar, dome-like or other three-dimensional shape.

Figure 13:
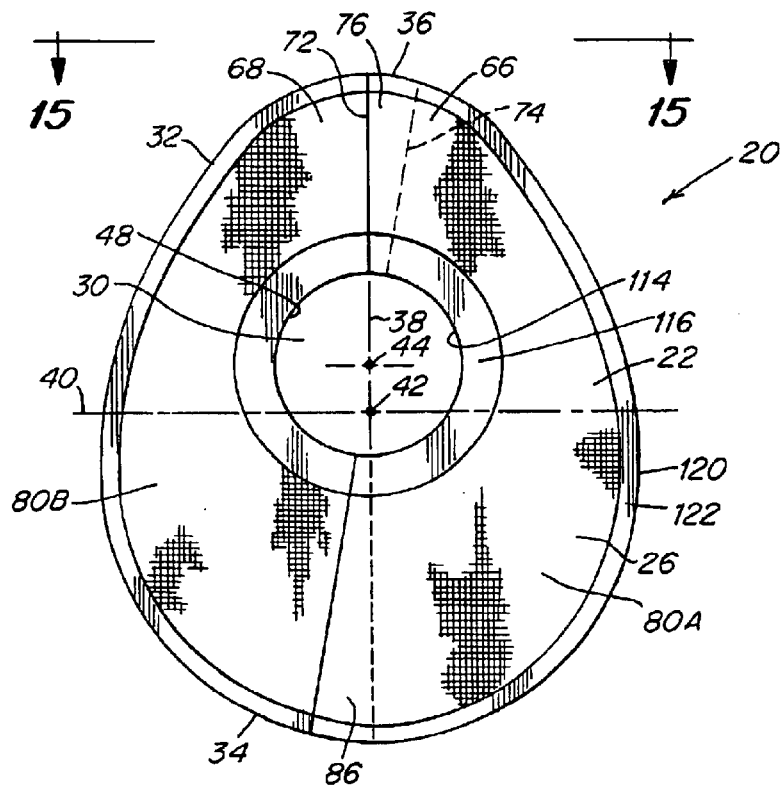
FIG. 13 is a top plan view of a prosthetic repair fabric in accordance with another illustrative embodiment of the present invention.
Figure 14:
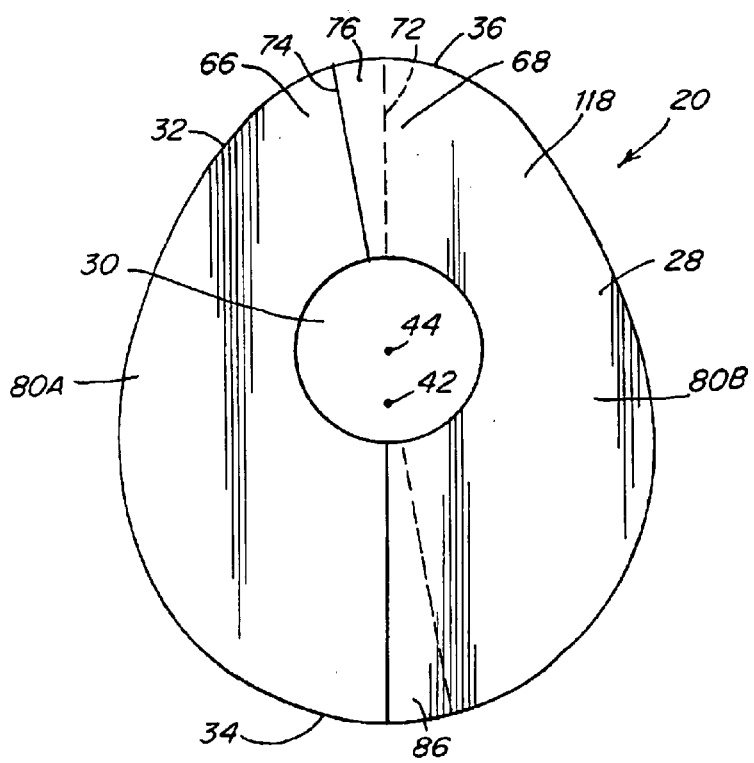
FIG. 14 is a bottom plan view of the prosthetic repair fabric of FIG. 13.
Figure 15:
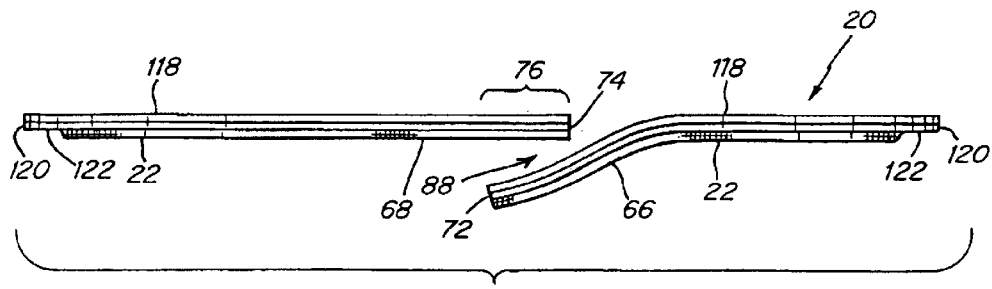
FIG. 15 is a side view of the prosthetic repair fabric taken along view line 15—15 of FIG. 13.
Figure 16:
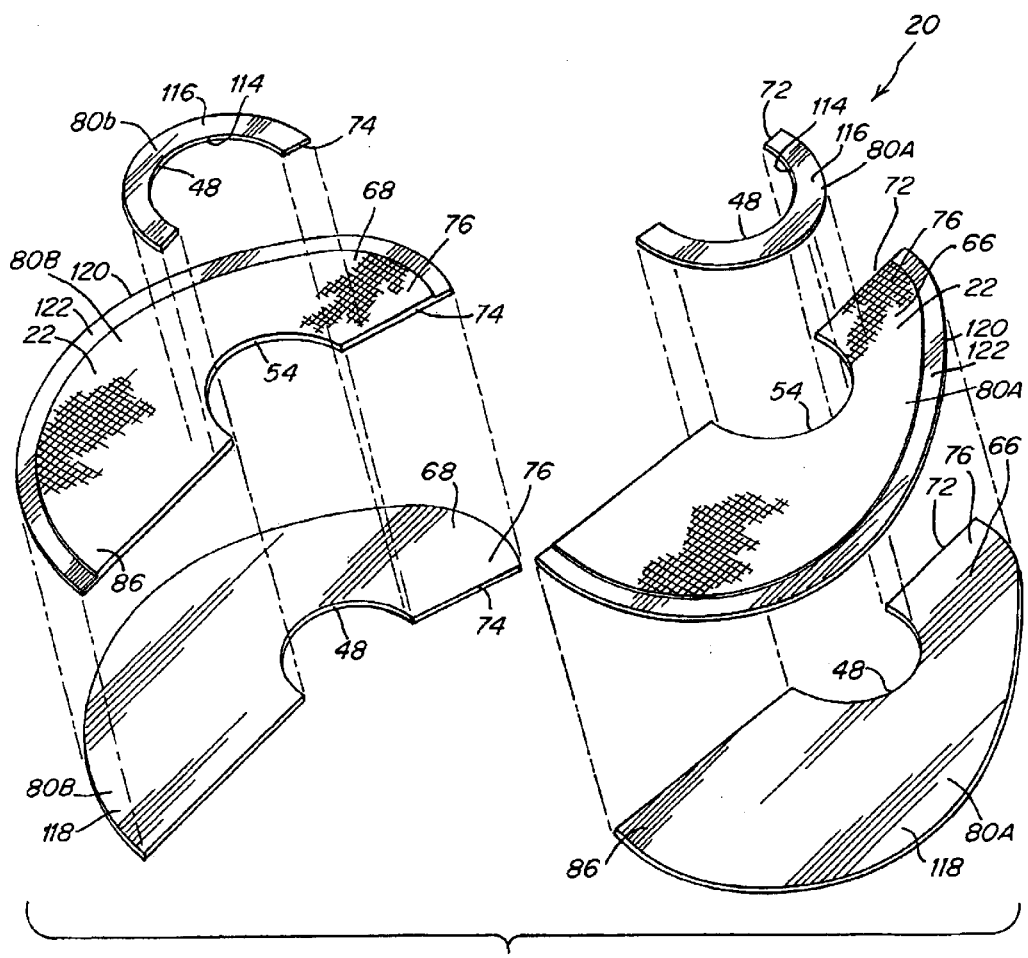
FIG. 16 is an exploded top perspective view of the prosthetic repair fabric of FIG. 13.
Figure 17:
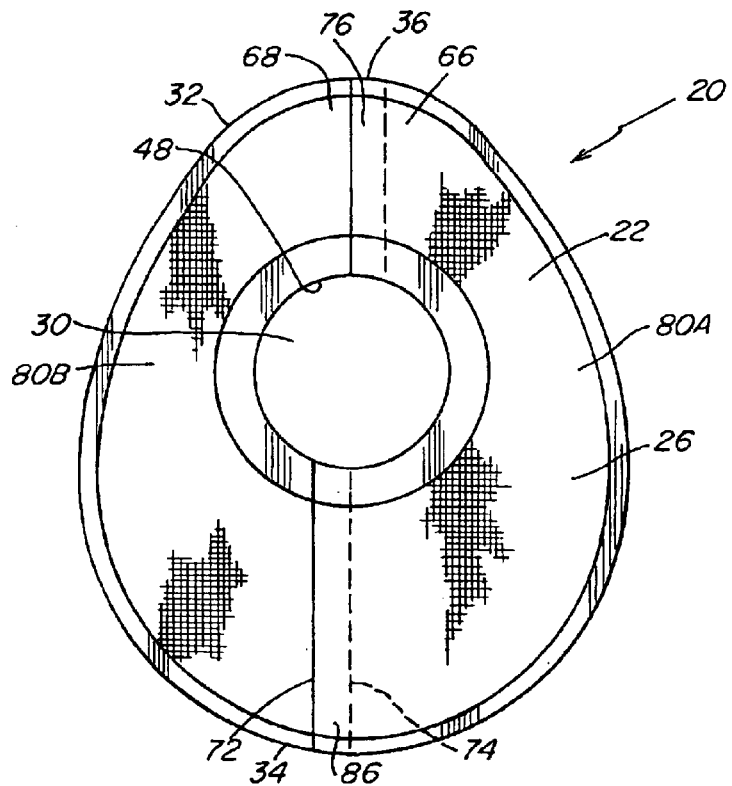
FIG. 17 is a top plan view of a prosthetic repair fabric in accordance with a further illustrative embodiment of the invention.

The size and shape of the overlap area 76 of the tails 66, 68 may be selected to provide an adequate area for fastening the tails 66, 68 together. As illustrated in FIG. 13, the overlap area has a wedge shape, being narrower towards the opening 30 and wider towards the outer periphery 32. It is to be appreciated that other overlap shapes may be implemented with the prosthesis. For example, the wedge shape could be inverted from the configuration shown, with the end toward the opening being wider than the end of the overlap closer to the outer edge of the implant. In one embodiment where the tails may be sutured to one another, the overlap area 76 may be at least approximately 1 cm wide at its smallest dimension, and may be overlapped to be approximately 2–3 cm wide. In another illustrative embodiment shown in FIG. 17, the overlap area 76 has a substantially uniform width. Of course, any suitable shapes and sizes of the overlapping area may be employed with the implant.

Similar to the various embodiments described above, this illustrative prosthesis may include a tissue infiltratable layer and one or more barriers to isolate selected portions of the fabric from regions of potential adhesion. For example, any one or combination of the inner opening edge, the inner margin, the outer peripheral edge, the outer margin, the edges of the slit, the margin adjacent the slit, and the surface facing the viscera, may include a barrier that is resistant to adhesion formation. The barriers may include a barrier type fabric as well as a tissue infiltratable fabric that has been selectively rendered adhesion resistant. Alternatively, the implant may be formed completely of a barrier material.

To facilitate the fabrication of a prosthesis with an overlap region, the prosthesis 20 may be formed from two or more separate sections. In the illustrative embodiment shown in FIGS. 13–16, the prosthesis 20 includes first and second segments 80A, 80B that are joined to each other to form the implant. As illustrated, each segment is generally C-shaped and includes first and second end portions with a curved mid-portion. The first and second segments are arranged with the first and second end portions of the first segment overlapping the first and second end portions of the second segment to form the prosthesis with first and second overlap areas 76, 86. When combined, the first and second segments form the body portion of the prosthesis with an opening 30 for receiving the esophagus or other tube-like structure. In this manner, a portion of the outer periphery of each segment forms the outer periphery of the implant and a portion of the inner periphery of each segment forms the opening.

In the illustrative embodiment, each segment includes a tissue infiltratable fabric layer 22 and a surface barrier layer 118 that covers the surface of the fabric layer that will face the abdominal viscera. Each segment also includes an inner edge barrier 114 along the opening edge to reduce the incidence of adhesions to the esophagus. A margin barrier 116 is provided on a portion of the first surface surrounding the opening. An outer edge barrier 120 is provided along the outer edge of the fabric layer to reduce the likelihood of adhesion formation at the periphery of the implant. An outer margin barrier 122 is also provided along the outer margin of the fabric adjacent the outer periphery of the first side of the prosthesis. It is to be understood that the prosthesis may include, if even desired, any one or combination of these or other barriers to accommodate any particular repair procedure.

As illustrated, each of the first and second segments 80A, 80B extends more than 180 degrees about the outer periphery of the implant to ensure that the segments provide a sufficient amount of material at their respective first and second end portions to create the overlap areas. The mid-portion areas are configured to separate the overlap areas 76, 86 by more than approximately 90 degrees of the outer periphery of the implant. In the embodiment shown in FIGS. 13–16, each mid-portion area extends approximately 170 degrees of the outer periphery of the implant and each overlap area extends approximately 10 degrees of the outer periphery of the implant. It is to be appreciated that each segment 80A, 80B may have any suitable asymmetric or symmetric shape and may form any suitable amount of the outer circumference 32 of the prosthesis 20 and the inner circumference 48 of the opening 30. For example, a mid-portion of one or both segments may be configured to form 90 degrees or more of the outer periphery of the prosthesis, or 120 degrees or more of the outer periphery.

Figure 18:
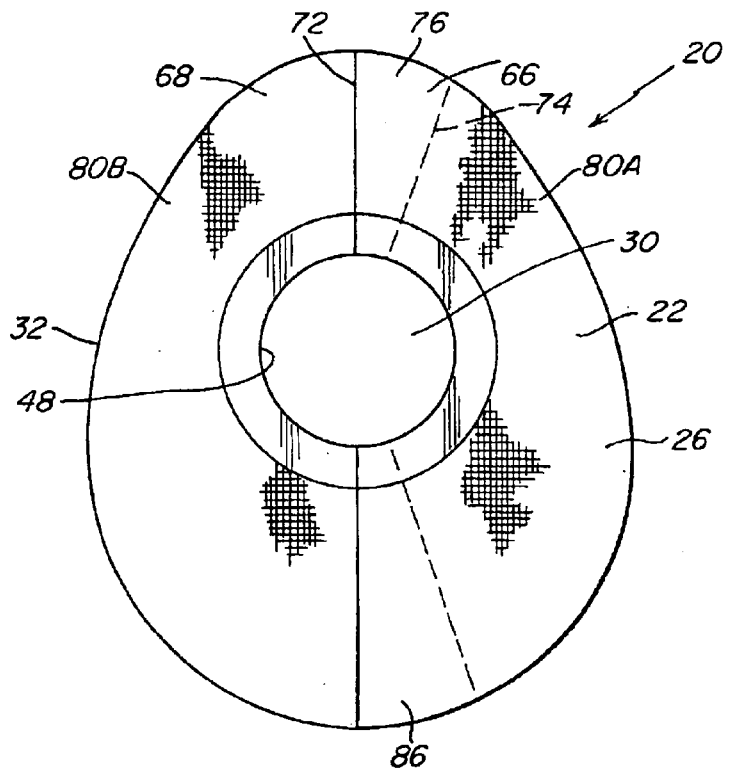
FIG. 18 is a top plan view of a prosthetic repair fabric in accordance with another embodiment of the present invention.

In another illustrative embodiment shown in FIG. 18, the first segment 80A forms approximately 180 degrees of the inner circumference 48 and the outer circumference 32 of the prosthesis 20, and the second segment 80B forms greater than 180 degrees of the inner circumference 48 and the outer circumference 32 of the prosthesis 20 to form the overlap areas 76, 86.

In the illustrative embodiments of FIGS. 13–18, the first and second segments are joined to each other at the second overlap area so as to configure the prosthesis with a pair of tails 66, 68 at the first overlap area 76 that may be opened to receive the esophagus into the opening. The second overlap area 86 is located approximately 180 degrees from the first overlap,area 76 with the tails. Thus, in these embodiments, the second overlap area 86 is located at the obtuse end 34 of the implant, and the first overlap area 76 is located at the acute end 36 of the implant. It is to be understood that the overlap areas 76, 86 may extend from the periphery 32 of the prosthesis 20 to the opening 30 from any suitable direction and have any angular separation as would be apparent to one of skill in the art.

Figure 19:
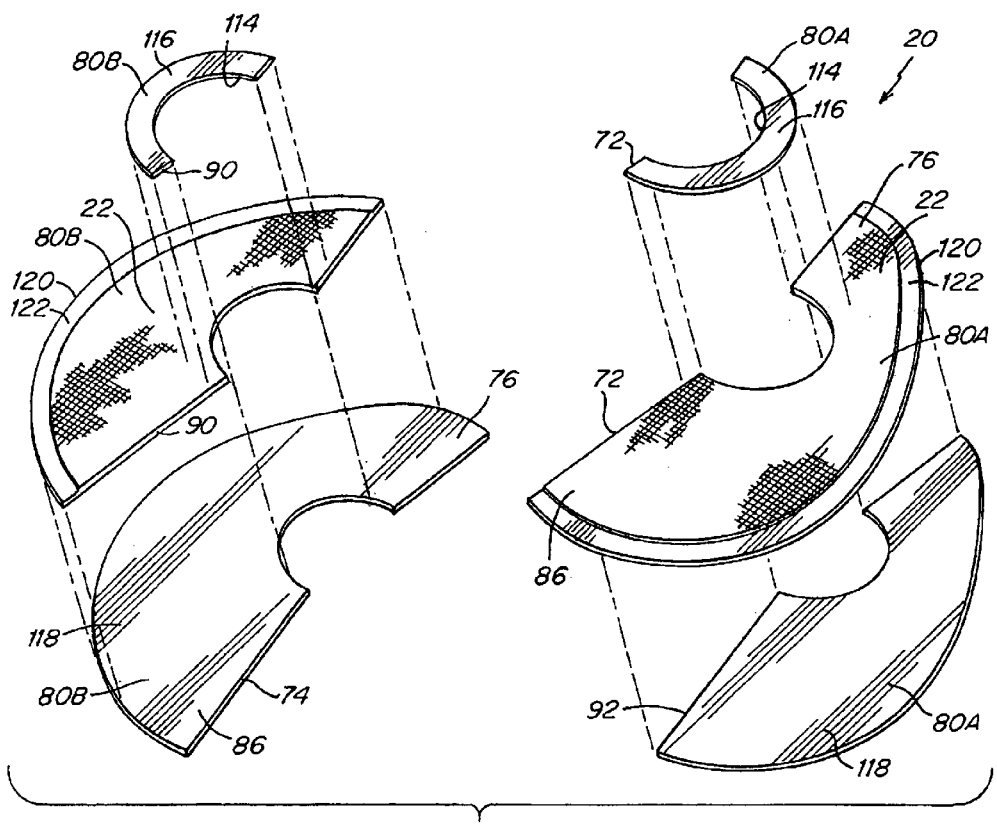
FIG. 19 is an exploded top perspective view of a prosthetic repair fabric in accordance with another illustrative embodiment of the invention.
Figure 20:
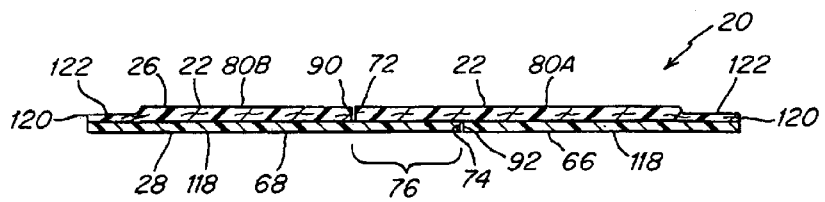
FIG. 20 is a cross-sectional view of the prosthetic repair fabric of FIG. 19 taken along a section line similar to section line 4—4 of FIG. 1.
Figure 21:
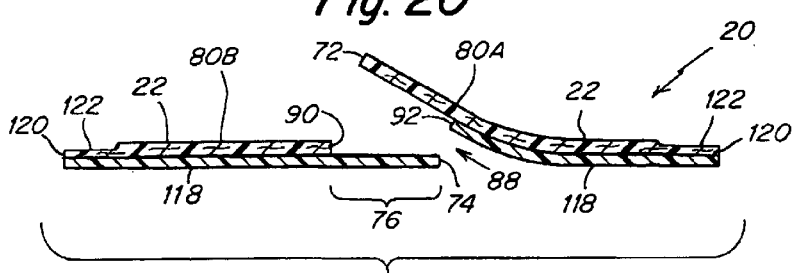
FIG. 21 is the cross-sectional view of the prosthetic repair fabric of FIG. 20 illustrating the open access passage.

When fabricating a prosthesis from multiple segments, such as described above, it may be desirable to maintain a uniform thickness across the overlap areas and the mid-portion areas of the segments. In one illustrative embodiment shown in FIGS. 19–21, he first and second end portions of the segments 80A, 80B are configured to nest with one another to form overlap areas having a thickness that approximates the thickness of the mid-portions. As shown in FIGS. 20–21, the first overlap area 76 includes an end portion 72 of the tissue infiltratable layer of the first segment 80A that extends beyond the end 92 of the surface barrier layer 118, and an end portion 74 of the surface barrier 118 of the second segment 80B that projects beyond the end 90 of the tissue infiltratable layer 22. The projecting end extensions 72, 74 may have the same length as shown, or may have different lengths so long as the dimensions allow the end extensions 72, 74 to nest with each other. The end portions of the first and second segments may be similarly configured at the second overlap area.

In some configurations, the segments may include multiple layers of materials having different thickness relative to each other. For example, each segment 80A, 80B may include a fabric layer 22 that is significantly thicker than a surface barrier 118 overlying the fabric layer. Eliminating a portion of the fabric layer from the end portion of one segment without removing a corresponding portion of the surface barrier from the end portion of the other segment may result in an overlap area having a thickness that may be only slightly thicker than the rest of the implant, such that the prosthesis essentially has a uniform thickness.

Figure 22:
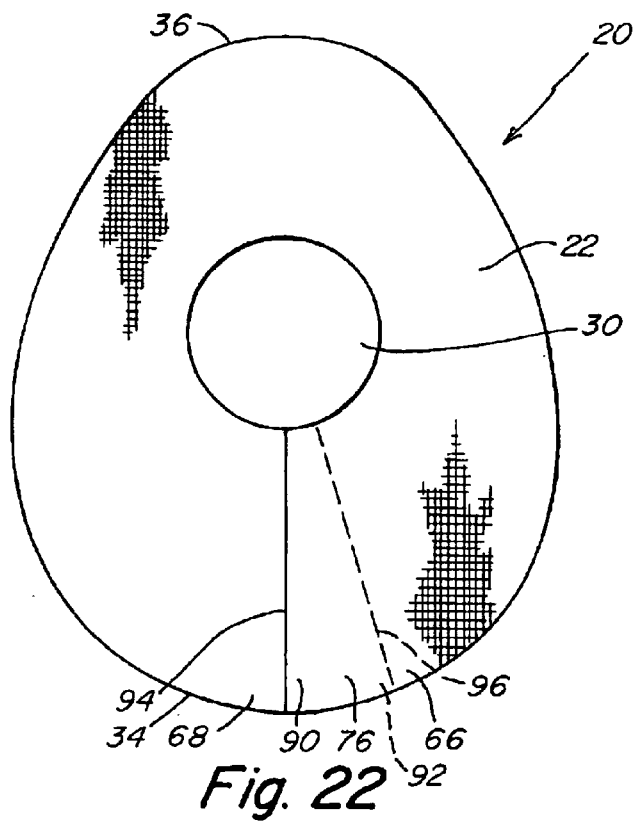
FIG. 22 is a top plan view of a prosthetic repair fabric in accordance with another illustrative embodiment of the present invention.

The prosthesis may be configured with a unitary body portion that includes a single overlap area for providing access to the opening for the esophagus. In one illustrative embodiment shown in FIG. 22, the body portion of the prosthesis includes a tissue infiltratable layer 22 and a surface barrier layer 118 (not shown) covering the viscera facing surface of the implant. The fabric layer 22 has a first slit 94 extending from the opening 30 to the outer periphery of the implant, while the surface barrier 118 has a second slit 96 extending from the opening to the outer periphery. As shown, the first and second slits are offset from each other. This slit arrangement results in a portion 90 of the fabric layer 22 extending beyond the surface barrier layer 118 on one tail 66 with a portion 92 of the barrier layer extending beyond the fabric layer on the other tail 68 to create an overlap area 76.

The tissue infiltratable fabric extension 90 and the surface barrier extension 92 nest with one another to maintain a uniform thickness for the implant. Lifting one extension relative to the other creates an access passage 88 for positioning the prosthesis about the esophagus. It is to be appreciated that the slits may extend to the opening 30 from any direction to locate the access passage at any suitable portion of the implant. As shown, the overlap area 76 is located at the obtuse end 34 of the implant, although it could be located at the acute end 36 to minimize the amount of stitching during the repair procedure and to place the surgical stitches away from the hiatal hernia.

Figure 23:
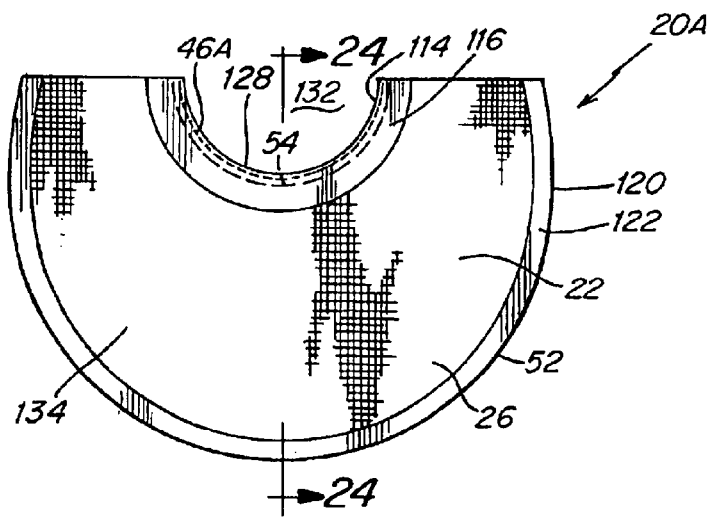
FIG. 23 is a top plan view of a prosthetic repair fabric in accordance with a further illustrative embodiment of the present invention.
Figure 24:
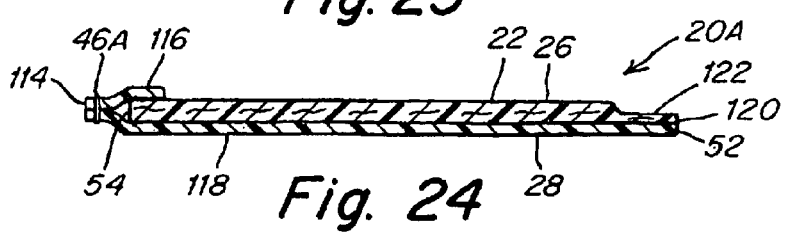
FIG. 24 is a cross-sectional view of the prosthetic repair fabric of FIG. 23 taken along section line 24—24.

In certain repair procedures it may be desirable to employ a prosthesis that extends about only a portion of the esophagus or other tube-like structure, rather than completely about the structure. In one illustrative embodiment shown in FIGS. 23–24, the prosthesis 20A has a partial annular shape configuration, similar in arrangement to the obtuse end of the implant described above. The prosthesis includes a body portion 134 that is configured to cover the defect, such as an enlarged or weakened hiatus. The prosthesis is provided with a partial opening 132 that is adapted to receive a portion of the esophagus. As shown, the body portion has a generally C-shape and the edge of the opening is defined by a semi-circular edge 128 of the body portion that is sized to receive a portion of the esophagus.

In the illustrative embodiment, the body portion includes a tissue infiltratable fabric layer 22, and a surface barrier layer 118 that covers the surface of the fabric layer that will face the abdominal viscera. The implant also includes an inner edge barrier 114 along the opening edge to reduce the incidence of adhesions to the esophagus. A margin barrier 116 is provided on a portion of the first surface surrounding the opening. An outer edge barrier is provided along the outer edge 52 of the fabric layer to reduce the likelihood of adhesion formation at the periphery of the implant. An outer margin barrier 122 is also provided along the outer margin of the fabric adjacent the outer periphery of the first side of the prosthesis. It is to be understood that the prosthesis may include, if even desired, any one or combination of these or other barriers to accommodate any particular repair procedure.

Figure 25:
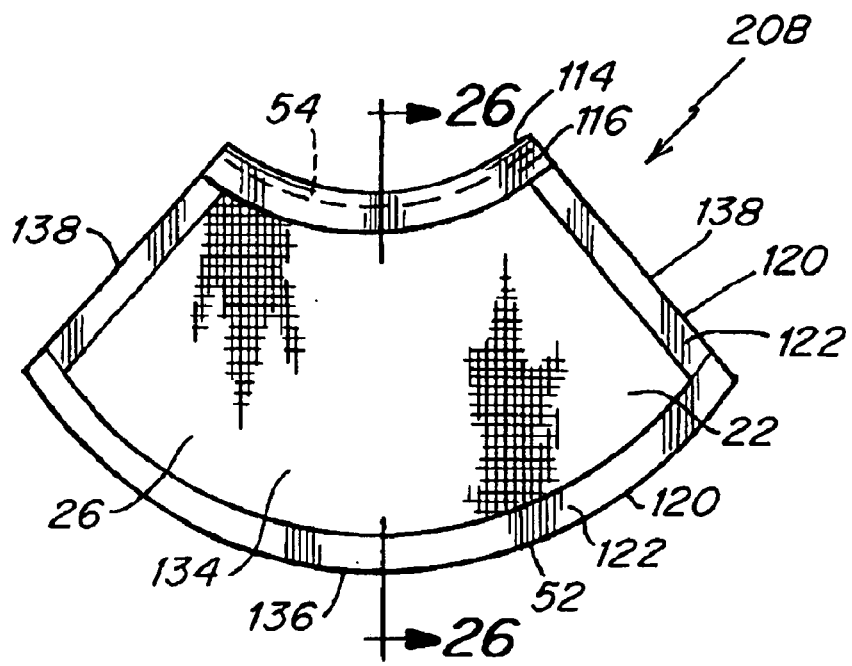
FIG. 25 is a top plan view of a prosthetic repair fabric in accordance with another illustrative embodiment of the present invention.
Figure 26:
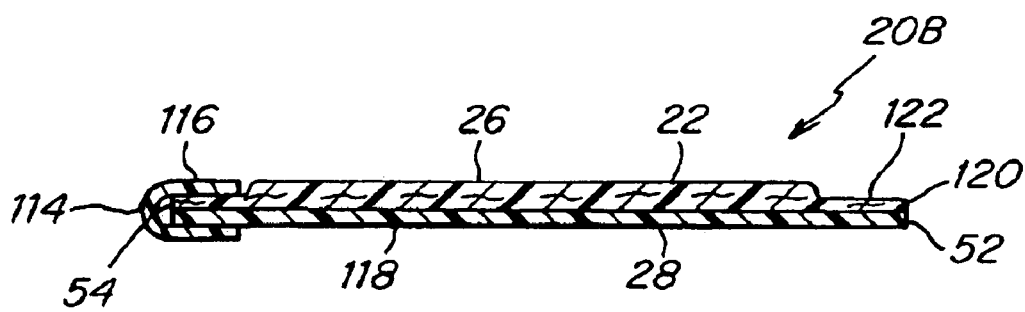
FIG. 26 is a cross-sectional view of the prosthetic repair fabric of FIG. 25 taken along section line 26—26.

Another illustrative embodiment of a prosthesis for repairing a hiatal hernia is shown in FIGS. 25–26. The prosthesis 20B includes a body portion 134 with a curved or partial annular shape that extends along an arc that is less than 180°. The body portion includes an outwardly curving bottom edge 136, an inwardly curving top edge 54 and a pair of side edges 138 that are angled so as to converge toward each other from the bottom edge toward the top edge. The top edge 54 forms a partial opening that is configured to receive and conform to the wall of the esophagus.

The body portion includes a tissue infiltratable fabric layer 22 and a surface barrier 118 similar to those described above. The prosthesis also includes outer edge barriers 120 and outer margin barriers 122 along the bottom edge 136 and the side edges 138. The inner edge 54 is isolated from the esophagus or other tube-like structure with an inner edge barrier 114 and an inner margin barrier 116. It is to be understood that any one or combination of these or other barriers may be implemented with the prosthesis as would be apparent to one of skill in the art.

In the illustrative embodiment shown in FIG. 26, the inner edge barrier 114 includes a continuous barrier cuff that wraps completely about the inner edge. In this regard, the cuff extends continuously from the inner margin of the fabric layer 22 to form the inner margin barrier 116, across the inner edge 54, and onto a portion of the surface barrier 118 adjacent the edge. Of course, any suitable edge barrier configuration may be implemented with the prosthesis.

Figure 27:
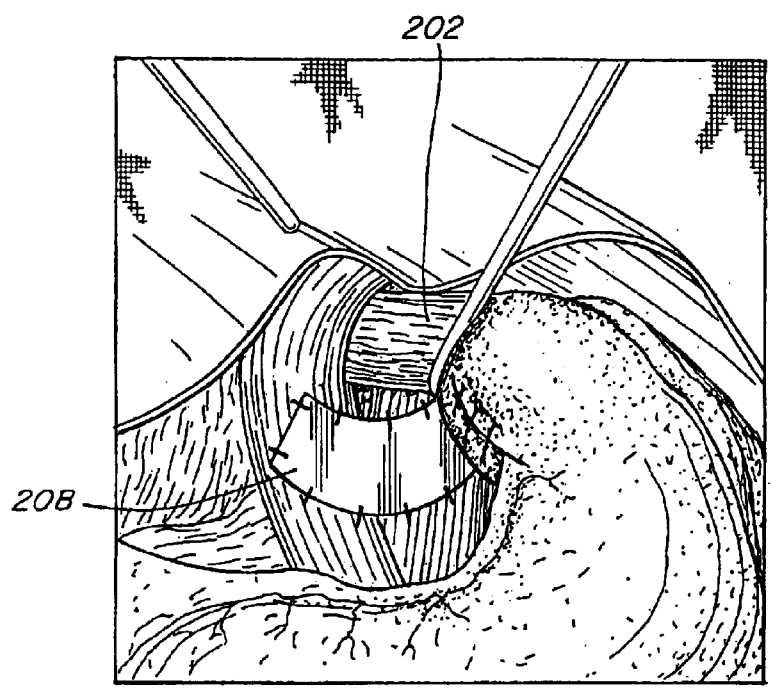
FIG. 27 is a schematic view illustrating the prosthetic repair fabric of FIG. 25 attached to the crura of the diaphragm proximate to the esophagus to repair a hernia in a tension-free repair.
Figure 28:
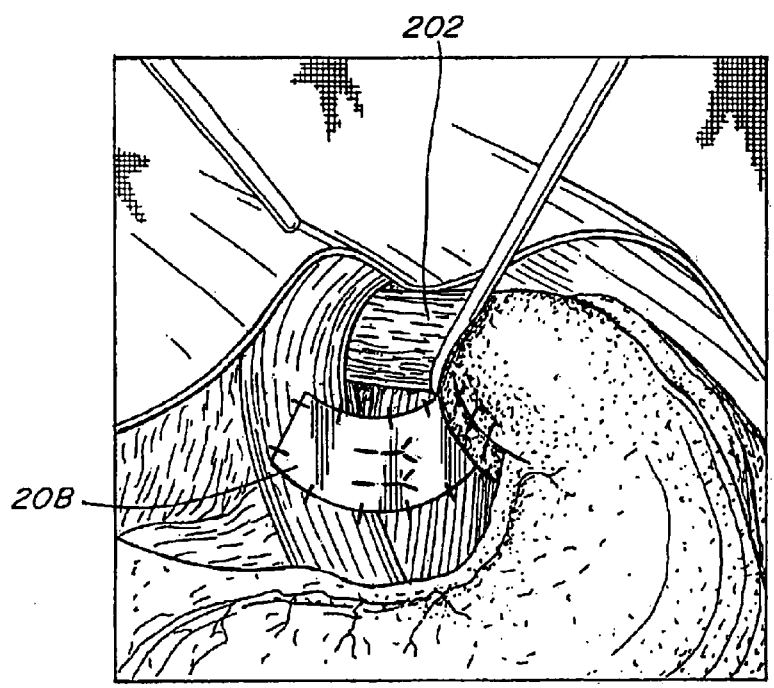
FIG. 28 is a schematic view illustrating the prosthetic repair fabric of FIG. 25 attached to the crura of the diaphragm to reinforce the sutures of a cruroplasty procedure.

FIGS. 27–28 illustrate several representative applications of the prosthesis of FIGS. 25–26 in the repair of a hiatal hernia. As shown in FIG. 27, the prosthesis 20B may be placed over the defect, without approximating the tissue, thereby effecting the repair in a substantially tension free manner. As shown in FIG. 28, the prosthesis may be employed in conjunction with a cruroplasty to reinforce the stitches with tissue infiltration over a surface area to alleviate the likelihood of suture pull-out when a force is applied to the crura, that otherwise potentially could lead to recurring herniation. It is to be understood that the prosthesis may be employed in any suitable manner for other repair procedures as would be apparent to one of skill.

Surgical treatment of GERD may include a fundoplication where the fundus is wrapped around the lower esophagus to recreate or reinforce the LES. In some instances, it may be desirable to employ a prosthesis in a fundoplication, such as a laparoscopic Nissen fundoplication, to secure the wrapped fundus itself or to cover and augment a repair maintained by other fastening mechanisms such as sutures, staples and the like. A prosthesis indicated for a fundoplication may be suitably shaped to fit the particular anatomy.

Figure 29:
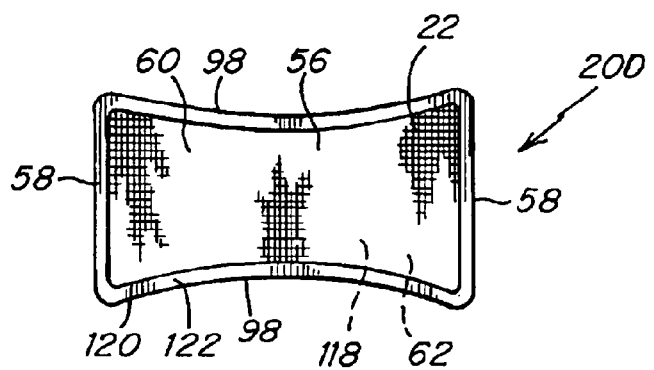
FIG. 29 is a top plan view of a prosthetic repair fabric in accordance with another illustrative embodiment of the present invention.

In one illustrative embodiment shown in FIG. 29, a prosthesis 20D includes a body with a middle section 56 and a pair of end portions 58 that extend from opposite sides of the middle section in a longitudinal direction. The middle section is narrower or of lesser width than the end portions 58 of the body. As shown, the end portions 58 are flared to provide additional surface area away from the middle section for tissue ingrowth. The body includes top and bottom edges 98 that curve toward each other in a direction from the flared ends 58 toward the middle section 56. Rather than curved edges, the top and bottom edges may include straight segments that extend linearly from an intermediate point of each edge toward the body ends. As shown, the prosthesis has a generally bow tie or butterfly shape, although any suitable shape may be employed for a fundoplication patch. For example, the prosthesis may be configured with a rectangular, oval, hour glass or other shape apparent to one of skill in the art.

The prosthesis 20D includes a body portion with a first surface 60 for facing the fundus of the stomach at the site of the fundoplication, and a second surface 62 for facing the abdominal cavity. The body portion includes a tissue infiltratable fabric 22 that forms the first surface 60 of the implant and a surface barrier layer 118 that forms the second surface 62 of the prosthesis. Since the stomach is a particularly sensitive organ, it may be desirable to use tissue infiltratable materials that are less aggressive and/or semi-permanent, such as collagen or PTFE mesh. The prosthesis 20D may also include one or more edge and/or margin barriers 120, 122 around the outer periphery and outer margin of the prosthesis, as discussed above. In another embodiment, the prosthesis 20D may be made entirely of a barrier material.

In one embodiment, the prosthesis 20D has a length of approximately 6.5 cm in a direction along the longitudinal axis, a width of approximately 3 cm at its narrow middle section 56, and a width of approximately 4 cm at the flared end portions 58. It is to be understood that these dimensions are exemplary and that the prosthesis 20D may be configured in any suitable size for buttressing, or replacing, the sutures of a fundoplication.

Figure 30:
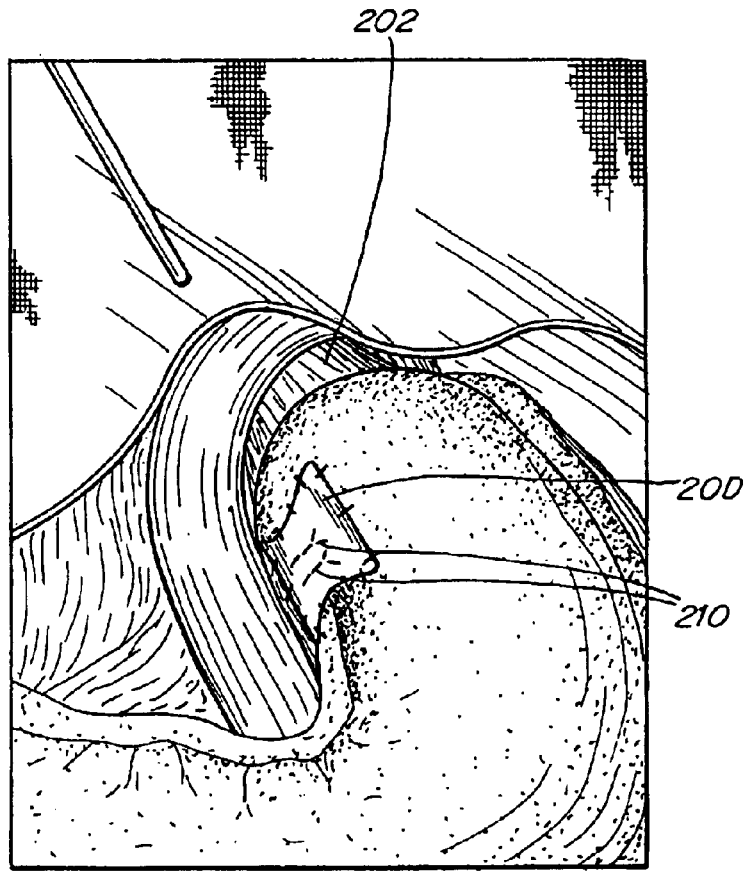
FIG. 30 is a schematic view illustrating the prosthetic repair fabric of FIG. 29 attached to the fundus of the stomach to reinforce a fundoplication procedure.
Figure 31:
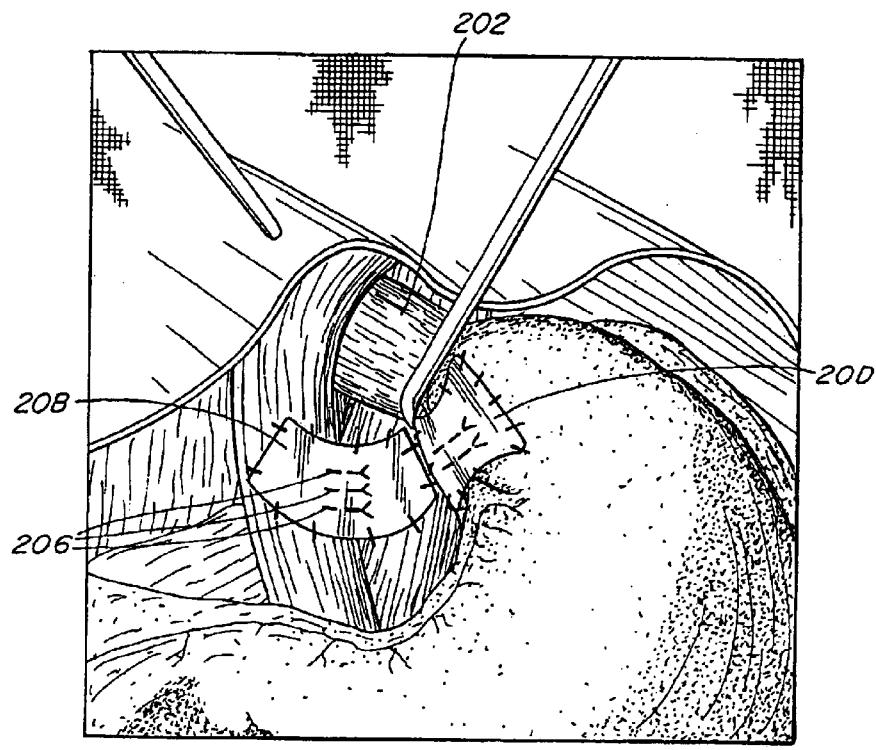
FIG. 31 is a schematic view illustrating the prosthetic repair fabric of FIG. 29 implanted to reinforce the sutures of a fundoplication in conjunction with the prosthetic repair fabric of FIG. 25 implanted to reinforce the sutures of a cruroplasty.
Figure 32:
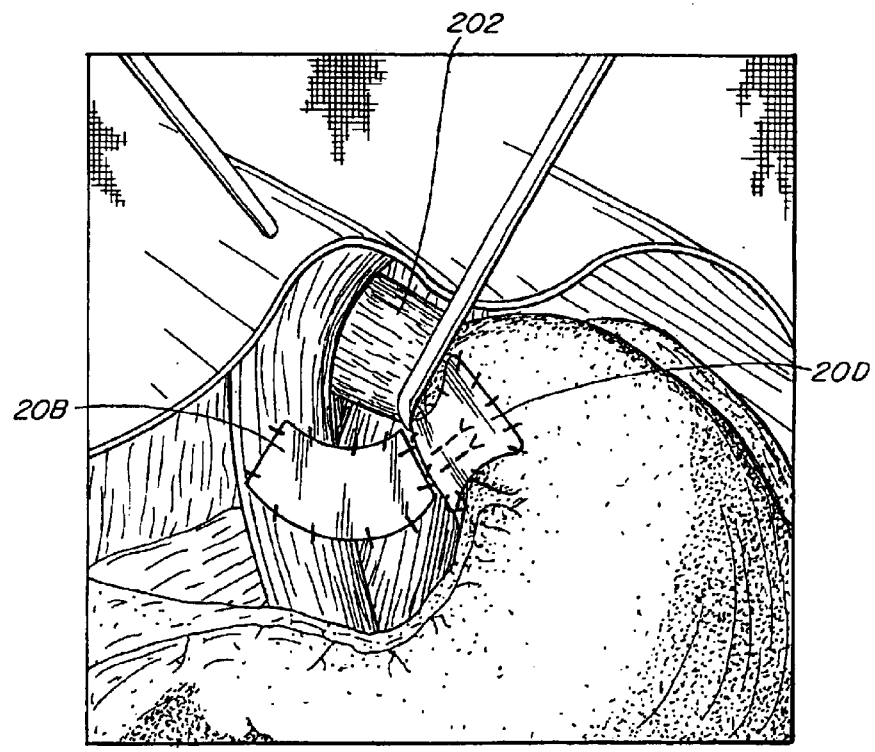
FIG. 32 is a schematic view illustrating the prosthetic repair fabric of FIG. 29 implanted to reinforce the sutures of a fundoplication in conjunction with the prosthetic repair fabric of FIG. 25 implanted to repair a hiatal hernia in a tension-free repair.

FIGS. 30–32 illustrate several representative applications of one or more prostheses in the repair of a hiatal hernia, reinforcing a cruroplasty and/or reinforcing a fundoplication. As shown in FIG. 30, the prosthesis 20D of FIG. 29 may be placed over a portion of the stomach to reinforce the sutures 210 of a fundoplication. As shown in FIG. 31, a fundoplication patch 20D may be employed in conjunction with a hiatal hernia patch 20B which is reinforcing the stitches 206 of a cruroplasty. FIG. 32 illustrates a prosthesis 20D reinforcing a fundoplication in combination with a prosthesis 20B implanted to repair a hiatal hernia in a tension-free manner. As is to be appreciated, any suitable combination of prostheses may be employed in the repair of one or more conditions and/or defects as would be apparent to one of skill in the art.

Figure 33:
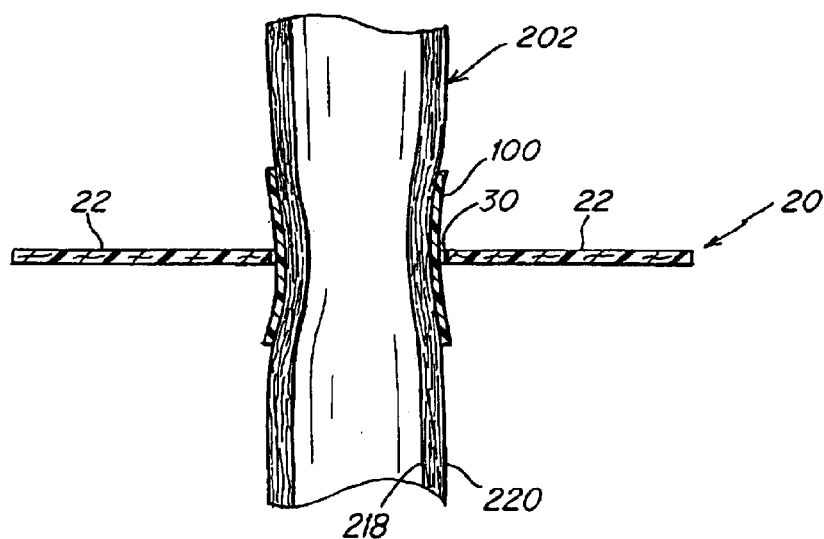
FIG. 33 is a schematic view of a prosthetic repair fabric in accordance with another embodiment of the invention.
Figure 34:
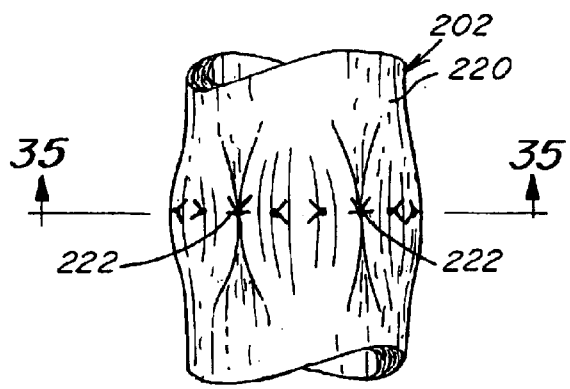
FIG. 34 is a schematic view a plication method in accordance with one illustrative embodiment of the present invention.

In some repair procedures, it may be desirable to not only repair a defect, such as a hiatal hernia, but also to combat GERD which can occur in a patient that has a hiatal hernia. To treat GERD, the internal diameter of the esophagus may be narrowed or reduced, so as to limit the flow of stomach fluid up into the esophagus. In one illustrative embodiment shown in FIG. 33, a cuff 100 is separately wrapped around the esophagus 202 to reduce the diameters of its external wall 220 and the internal wall 218. As illustrated, the cuff may be wrapped about the portion of the esophagus extending through a prosthesis 20 that is employed to repair the defect in a manner as described above. In this arrangement, not only does the cuff aid in combating GERD, but it also acts as barrier between the prosthesis and the esophagus.

Since it is desirable to avoid unduly constricting the walls of the esophagus so as not to interfere with its function, the cuff may be formed from a material that is expandable or otherwise allows the esophagus to expand, such as during swallowing and the like. In one embodiment, the cuff may be formed from a collagen mesh, fabric or film, although any suitable material may be used as would be apparent to one of skill in the art. The cuff or wrap 100 may be cross-linked and may incorporate into the wall of the esophagus 202, if desired.

Rather than a separate cuff to combat GERD, it may be desirable to employ a cuff or wrap that is integral with a prosthesis for repairing the defect. In one embodiment (not shown), the cuff may be provided as part of a prosthesis, such as a prosthesis similar to that described above for FIGS. 1–6. The cuff may be provided proximate the opening of the prosthesis so that it may be wrapped and secured about the esophagus as it passes through the opening to decrease the inner diameter of the LES. One or more fasteners may be provided to secure the cuff about the esophagus once the desired esophageal narrowing has been achieved.

Since GERD can occur in a patient that has a hiatal hernia, it may be desirable to treat GERD during a hiatal hernia repair. More particularly, a surgeon may find it advantageous to treat GERD during the repair of a hiatal hernia using a laparoscopic procedure.

Figure 35:
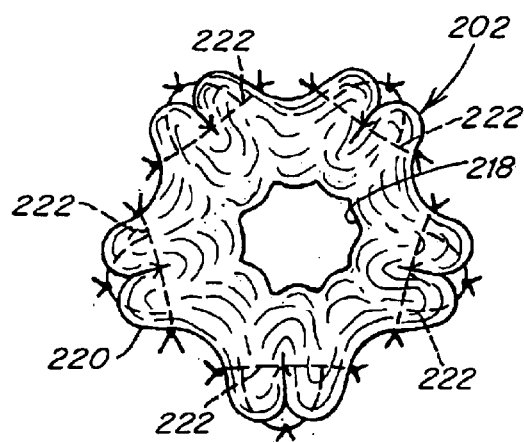
FIG. 35 is a cross-sectional view illustrating the plication method of FIG. 34 taken along section line 35—35.
Figure 36:
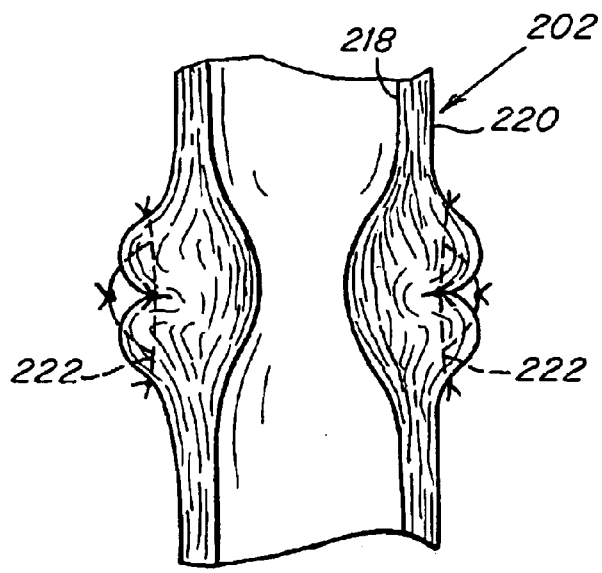
FIG. 36 is a schematic view of a plication method in accordance with another illustrative embodiment of the present invention.

In one illustrative embodiment of the invention as shown in FIGS. 35–36, one or more external plications or pleats are formed on the external wall 220 of the esophagus 202, such as along the LES, to reduce the inner diameter of the internal wall 218 of the esophagus 202 so as to lower the incidence of GERD. The plications are configured to extend in a longitudinal direction along the length of the esophagus 202, although any suitable configuration may be implemented. For example, in another illustrative embodiment shown in FIG. 36, the plications 222 may be formed laterally around the circumference of the esophagus 202. While FIGS. 34–37 illustrate external plications, it should be understood that the plications may be formed on the internal wall 218 of the esophagus 202. It is to be appreciated that the plications 222 may be formed using any suitable method apparent to one of skill in the art including, but not limited to, suturing, stapling, clipping, and tacking.

Figure 37:
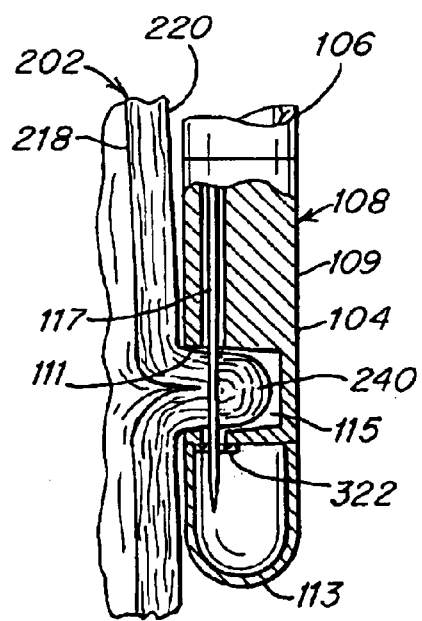
FIG. 37 is a schematic view of a cinch mechanism in accordance with one embodiment of the present invention with the needle deployed.

In one illustrative embodiment shown in FIG. 37, one or more plications 222 are formed with a cinch tool 108 configured to create folds in the esophagus 202. The cinch tool 108 may be attached at the end of an endoscope or laparoscope 106 to allow the surgeon to visualize the tissue that is to be pleated during a minimally invasive endoscopic or laparoscopic procedure. During a laparoscopic repair of a condition such as a hiatal hernia, the plications 222 are placed on the external wall 220 of the esophagus 202 to avoid a separate endoscopic procedure to the inner walls 218 of the esophagus 202.

As shown in FIG. 37, the cinch tool 108 includes a capsule housing 109 with a suction orifice 111 located on a side wall 104 of the capsule. The suction orifice 111 is to be fluidly connected to a suction device (not shown) at the opposite end of the endoscope or laparoscope 106. The capsule housing 109 is approximately 8–10 mm long and has a cylindrical shape with a rounded end cup 113 to reduce any sharp edges that may potentially damage surrounding tissue. It is to be understood that many other housing shapes, sizes and arrangements may be employed for the tool.

As the surgeon directs the capsule housing 109 against the esophageal tissue 202 to be plicated, the suction device is activated to draw a fold 240 of LES tissue into an internal chamber 115 of the capsule through the orifice 111. When adequate tissue purchase is attained, preferably 3–5 mm thick, the surgeon activates a needle 117 that pierces the folded tissue 240 and extends into the end cap 113 to deploy a suture tag 322. The needle 117 is retracted with the suture tag captured in the end cap, and the tool is withdrawn from the patient. Once withdrawn, the end cap 113 is removed to release the suture tag 322 which is then reloaded into the needle. The cinch tool 108 is then reintroduced and placed against another region of the tissue to repeat the process of folding and suturing the tissue.

After removal of the cinch 108 from the patient, the suture may be cut to remove the tag and eliminate excess suture length. A knot pusher (not shown) may be used to tie the suture with one or more half hitches, preferably a minimum of 5 half hitches. Once the knots are secure, a suture cutter (not shown) may be employed to cut the sutures. Thus, a plication 222 is formed by cinching together two folds 240 of LES tissue.

Although the illustrative embodiment describes forming a plication from two folds, it is to be appreciated that a plication may include any number of folds as would be apparent to one of skill in the art. For example, a plication may include a single fold or three or more folds that have been cinched together. Additionally, individual plications formed on the external wall of the esophagus may include different numbers of folds relative to other plications.

In one embodiment, the cinch tool 108 is a BARD ENDOCINCH endoscopic suturing system available from C. R. Bard, Inc. Although developed as an endoscopic cinch tool the ENDOCINCH can be used laparoscopically, according to one embodiment of the invention, to plicate the external wall 220 of the esophagus 202 to decrease the inner diameter 218 of the LES 216 to combat GERD.

The internal diameter 218 of the LES may also be reduced using other suitable methods apparent to one of skill. In one embodiment, RF energy or cryotherapy may be applied to shrink the external and internal diameter of the esophagus 202. In another embodiment, a bulking agent may be injected into the wall of the LES to increase the external diameter 220 and reduce the internal diameter 218 of the LES. Those skilled in the art will recognize that many methods and prostheses may be appropriate for decreasing the internal diameter 218 of the LES and/or increasing the external diameter 220 of the LES.

It should be understood that the foregoing descriptions of various embodiments of the invention are intended merely to be illustrative thereof and that other embodiments, modifications, and equivalents of the invention are within the scope of the invention recited in the claims appended hereto.

What is claimed is:

1. An implantable prosthesis for repairing a tissue or muscle wall defect located near the esophagus, the implantable prosthesis comprising:

a layer of repair fabric that is susceptible to the formation of adhesions with tissue and organs, the layer of repair fabric including first and second surfaces and at least one fabric edge extending from the first surface to the second surface, the first surface adapted to face the tissue or muscle wall defect when the implantable prosthesis is placed in a patient near the esophagus, the second surface adapted to face away from the tissue or muscle wall defect and toward the patient's cavity viscera, the layer of repair fabric having an opening that is adapted to receive the esophagus;

a surface barrier that inhibits the formation of adhesions with tissue and organs, the surface barrier being disposed on at least a portion of the second surface of the layer of repair fabric to inhibit the formation of adhesions between the portion of the second surface and adjacent tissue and organs when the implantable prosthesis is placed in the patient; and at least one edge barrier that inhibits the formation of adhesions with tissue and organs, the at least one edge barrier extending about at least a portion of the at least one fabric edge to inhibit the formation of adhesions between the portion of the at least one fabric edge and adjacent tissue and organs.

2. The implantable prosthesis according to claim 1, wherein the at least one fabric edge includes an opening edge that defines the opening in the layer of fabric, and wherein the at least one edge barrier includes an opening edge barrier that extends about the opening edge to inhibit the formation of adhesions between the opening edge and the esophagus.

3. The implantable prosthesis according to claim 2, wherein the opening edge barrier includes at least one barrier layer that overlies the opening edge.

4. The implantable prosthesis according to claim 3, wherein the at least one barrier layer further extends onto a portion of the second surface adjacent the opening.

5. The implantable prosthesis according to claim 4, wherein the at least one barrier layer further extends onto a portion of the first surface adjacent the opening.

6. The implantable prosthesis according to claim 5, wherein the opening edge barrier is an integral extension of the surface barrier that is wrapped about the opening edge.

7. The implantable prosthesis according to claim 3, wherein the at least one barrier layer includes first and second barrier layers, the first barrier layer being disposed on a margin of the first surface adjacent the opening and extending beyond the opening edge, the second barrier layer being disposed on a margin of the second surface adjacent the opening and extending beyond the opening edge to overlie the first barrier layer, portions of the first and second barrier layers extending beyond the opening edge being attached directly to each other to isolate the opening edge.

8. The implantable prosthesis according to claim 2, wherein the at least one fabric edge further includes an outer peripheral edge, and wherein the at least one edge barrier further includes an outer edge barrier that extends about at least a portion of the outer peripheral edge to inhibit the formation of adhesions between the portion of the outer peripheral edge and adjacent tissue or organs.

9. The implantable prosthesis according to claim 2, wherein the opening edge barrier defines a prosthesis opening that has a diameter of approximately 2.5 cm to approximately 4.5 cm.

10. The implantable prosthesis according to claim 9, wherein the prosthesis opening has a diameter of approximately 2.5 cm to approximately 3.5 cm.

11. The implantable prosthesis according to claim 9, wherein the prosthesis opening has a diameter of approximately 3.5 cm to approximately 4.5 cm.

12. The implantable prosthesis according to claim 1, wherein the at least one edge barrier includes a barrier layer that wraps about the at least one fabric edge from a margin of the first surface adjacent the fabric edge to a margin of the second surface adjacent the fabric edge.

13. The implantable prosthesis according to claim 1, wherein the at least one fabric edge includes an outer peripheral edge, and wherein the at least one edge barrier includes an outer edge barrier that extends about at least a portion of the outer peripheral edge to inhibit the formation of adhesions between the portion of the outer peripheral edge and adjacent tissue or organs.

14. The implantable prosthesis according to claim 13, wherein the outer edge barrier includes a portion of the layer of repair fabric that has been altered to inhibit the formation of adhesions thereto.

15. The implantable prosthesis according to claim 1, wherein the at least one fabric edge includes an outer edge and a pair of slit edges that extend from the opening to the outer edge, and wherein the at least one edge barrier includes a slit barrier disposed about a portion of each of the slit edges.

16. The implantable prosthesis according to claim 15, wherein the slit barrier includes a portion of the layer of repair fabric along each slit edge that has been altered to inhibit the formation of adhesions thereto.

17. The implantable prosthesis according to claim 1, wherein the layer of repair fabric has a plurality of interstices that are constructed and arranged to allow tissue ingrowth.

18. The implantable prosthesis according to claim 1, wherein the layer of repair fabric includes an outer peripheral edge and an access passage that extends from the opening to the outer peripheral edge.

19. The implantable prosthesis according to claim 1, wherein the layer of repair fabric has an ellipsoid shape with a major axis and a minor axis, the layer of repair fabric being asymmetric about the minor axis and including an oblate end and an acute end.

20. The implantable prosthesis according to claim 19, wherein the opening has a center that is located along the major axis and between the minor axis and the acute end.

21. The implantable prosthesis according to claim 20, wherein the layer of repair fabric includes an outer peripheral edge and an access passage that extends from the opening to the outer peripheral edge.

22. The implantable prosthesis according to claim 21, wherein the access passage is located at the acute end.

23. The implantable prosthesis according to claim 1, wherein the layer of repair fabric is formed from one of polypropylene mesh and PTFE mesh.

24. The implantable prosthesis according to claim 1, wherein the at least one edge barrier is formed from ePTFE.

25. The implantable prosthesis according to claim 1, wherein the surface barrier is formed from ePTFE.

26. The implantable prosthesis according to claim 1, wherein the opening is a complete opening that is adapted to completely surround the esophagus when the implantable prosthesis is placed near the esophageal hiatus.

27. The implantable prosthesis according to claim 1, wherein the opening is a partial opening that is adapted to partially surround the esophagus when the implantable prosthesis is placed near the esophageal hiatus.

28. The implantable prosthesis according to claim 27, wherein the layer of repair fabric has a partial annular shape.

29. The implantable prosthesis according to claim 27, wherein the layer of repair fabric is C-shaped.

30. The implantable prosthesis according to claim 1, wherein the surface barrier is disposed on substantially the entire second surface.

31. An implantable prosthesis for repairing a tissue or muscle wall defect located near a tube-like structure, the implantable prosthesis comprising:
    a body portion that is constructed and arranged to be placed proximate the tissue or muscle wall defect, the body portion including an outer periphery and having an opening that is adapted to receive the tube-like structure, the body portion comprising:
      a layer of repair fabric that is susceptible to the formation of adhesions with tissue and organs, the layer of repair fabric including first and second surfaces and at least one fabric edge extending from the first surface to the second surface, the first surface adapted to face the tissue or muscle wall defect when the implantable prosthesis is placed in a patient near the tube-like structure, the layer of repair fabric having a first slit extending from the opening to the outer periphery to receive the tube-like structure in the opening;
      a surface barrier that inhibits the formation of adhesions, the surface barrier being disposed at the second surface of the layer of repair fabric to inhibit the formation of adhesions on the second surface when the implantable prosthesis is placed in the patient, the surface barrier having a second slit extending from the opening to the outer periphery to receive the tube-like structure in the opening, the second slit being offset from the first slit, the second slit overlying a portion of the layer of repair fabric and the first slit overlying a portion of the surface barrier.

32. The implantable prosthesis according to claim 31, wherein the body portion includes at least one edge barrier that inhibits the formation of adhesions with tissue and organs, the at least one edge barrier extending about at least a portion of the at least one fabric edge to inhibit the formation of adhesions between the portion of the at least one fabric edge and adjacent tissue and organs.

33. The implantable prosthesis according to claim 32, wherein the at least one edge barrier is formed from ePTFE.

34. The implantable prosthesis according to claim 32, wherein the at least one edge barrier includes a barrier layer that wraps about the at least one fabric edge from a margin of the first surface adjacent the fabric edge to a margin of the second surface adjacent the fabric edge.

35. The implantable prosthesis according to claim 34, wherein the at least one fabric edge includes an opening edge that forms the opening, and wherein the at least one edge barrier includes an opening edge barrier that extends about the opening edge to inhibit the formation of adhesions between the opening edge and the tube-like structure.

36. The implantable prosthesis according to claim 32, wherein the at least one fabric edge includes an outer peripheral edge, and wherein the at least one edge barrier includes an outer edge barrier that extends about at least a portion of the outer peripheral edge to inhibit the formation of adhesions between the portion of the outer peripheral edge and adjacent tissue or organs.

37. The implantable prosthesis according to claim 31, wherein the body portion has an ellipsoid shape with a major axis and a minor axis, the body portion being asymmetric about the minor axis and including an oblate end and an acute end.

38. The implantable prosthesis according to claim 37, wherein the opening has a center that is located along the major axis and between the minor axis and the acute end.

39. The implantable prosthesis according to claim 31, wherein the layer of repair fabric has a plurality of interstices that are constructed and arranged to allow tissue ingrowth.

40. The implantable prosthesis according to claim 39, wherein the layer of repair fabric is formed from one of polypropylene mesh and PTFE mesh.

41. The implantable prosthesis according to claim 31, wherein the surface barrier is formed from ePTFE.

42. The implantable prosthesis according to claim 31, wherein the body portion is constructed and arranged to be placed proximate a patient's esophagus, the opening being adapted to receive the esophagus.

43. The implantable prosthesis according to claim 42, wherein the opening has a diameter of approximately 2.5 cm to approximately 4.5 cm.

44. The implantable prosthesis according to claim 43, wherein the opening has a diameter of approximately 2.5 cm to approximately 3.5 cm.

45. The implantable prosthesis according to claim 43, wherein the opening has a diameter of approximately 3.5 cm to approximately 4.5 cm.

46. An implantable prosthesis for repairing a tissue or muscle wall defect located near a tube-like structure, the implantable prosthesis comprising:

a body portion that is constructed and arranged to be placed proximate the tissue or muscle wall defect, the body portion including an outer periphery and having an opening that is adapted to receive the tube-like structure, the body portion comprising:
a layer of repair fabric that is susceptible to the formation of adhesions with tissue and organs, the layer of repair fabric including first and second surfaces, the first surface adapted to face the tissue or muscle wall defect when the implantable prosthesis is placed in a patient near the tube-like structure, the layer of repair fabric including an outer peripheral edge and an opening edge, the outer peripheral edge extending from the first surface to the second surface along the outer periphery, the opening edge extending from the first surface to the second surface along the opening; and a plurality of barriers that inhibit the formation of adhesions on selected portions of the layer of repair fabric when the implantable prosthesis is placed in the patient, the plurality of barriers including a surface barrier disposed on at least a portion of the second surface of the layer of repair fabric, a peripheral edge barrier disposed along at least a portion of the outer peripheral edge of the layer of repair fabric, and an opening edge barrier disposed along at least a portion of the opening edge of the layer of repair fabric.

47. The implantable prosthesis according to claim 46, wherein the surface barrier is disposed on substantially the entire second surface.

48. The implantable prosthesis according to claim 46, wherein the peripheral edge barrier extends along substantially the entire outer peripheral edge.

49. The implantable prosthesis according to claim 46, wherein the opening edge barrier extends along substantially the entire opening edge.

50. The implantable prosthesis according to claim 46, wherein the opening edge barrier includes a barrier layer that wraps about the opening edge from a margin of the first surface adjacent the opening edge to a margin of the second surface adjacent the opening edge.

51. The implantable prosthesis according to claim 46, wherein the layer of repair fabric has a slit extending from the opening to the outer periphery to receive the tube-like structure in the opening, the layer of repair fabric including a slit edge extending from the first surface to the second surface along the slit, and wherein the plurality of barriers includes a slit edge barrier disposed along at least a portion of the slit edge of the layer of repair fabric.

52. The implantable prosthesis according to claim 46, wherein the body portion has an ellipsoid shape with a major axis and a minor axis, the body portion being asymmetric about the minor axis and including an oblate end and an acute end.

53. The implantable prosthesis according to claim 52, wherein the opening has a center that is located along the major axis and between the minor axis and the acute end.

54. The implantable prosthesis according to claim 46, wherein the layer of repair fabric has a plurality of interstices that are constructed and arranged to allow tissue ingrowth.

55. The implantable prosthesis according to claim 54, wherein the layer of repair fabric is formed from one of polypropylene mesh and PTFE mesh.

56. The implantable prosthesis according to claim 46, wherein the surface barrier is formed from ePTFE.

57. The implantable prosthesis according to claim 46, wherein the opening edge barrier is formed from ePTFE.

58. The implantable prosthesis according to claim 46, wherein the body portion is constructed and arranged to be placed proximate a patient's esophagus, the opening being adapted to receive the esophagus.

59. The implantable prosthesis according to claim 58, wherein the opening has a diameter of approximately 2.5 cm to approximately 4.5 cm.

60. The implantable prosthesis according to claim 59, wherein the opening has a diameter of approximately 2.5 cm to approximately 3.5 cm.

61. The implantable prosthesis according to claim 59, wherein the opening has a diameter of approximately 3.5 cm to approximately 4.5 cm.

62. An implantable prosthesis for repairing a tissue or muscle wall defect located near a tube-like structure, the implantable prosthesis comprising:

a prosthetic repair fabric including an outer periphery and having an opening therein that is adapted to receive the tube-like structure, the prosthetic repair fabric including first and second segments, each of the first and second segments including a layer of fabric that is susceptible to the formation of adhesions with tissue and organs, each of the first and second segments including a first end and a second end, the first end of the first segment overlapping the first end of the second segment at a first overlap area, the second end of the first segment overlapping the second end of the second segment at a second overlap area, the first segment including a first mid-portion between the first and second overlap areas, the second segment including a second mid-portion between the first and second overlap areas, each of the first and second mid-portions forming a portion of the outer periphery of the prosthetic repair fabric that is greater than approximately 90 degrees.

63. The implantable prosthesis according to claim 62, wherein each of the first and second mid-portions forms a portion of the outer periphery of the prosthetic repair fabric that is equal to or greater than approximately 120 degrees.

64. The implantable prosthesis according to claim 63, wherein each of the first and second mid-portions forms a portion of the outer periphery of the prosthetic repair fabric that is approximately 170 degrees.

65. The implantable prosthesis according to claim 62, wherein each of the first and second segments includes a surface barrier that inhibits the formation of adhesions with tissue and organs, the surface barrier being disposed on a surface of the layer of fabric to inhibit the formation of adhesions between the surface and adjacent tissue and organs when the implantable prosthesis is placed in a patient.

66. The implantable prosthesis according to claim 65, wherein at least one of the first and second overlap areas is free of one of the layer of fabric and the surface barrier of at least one of the first and second segments.

67. The implantable prosthesis according to claim 65, wherein the surface barrier is formed from ePTFE.

68. The implantable prosthesis according to claim 62, wherein each of the first and second segments includes at least one fabric edge, each of the first and second segments including at least one edge barrier that inhibits the formation of adhesions with tissue and organs, the at least one edge barrier extending about at least a portion of the at least one fabric edge to inhibit the formation of adhesions between the portion of the at least one fabric edge and adjacent tissue and organs.

69. The implantable prosthesis according to claim 68, wherein the at least one edge barrier includes a barrier layer that wraps about the at least one fabric edge from a margin of the first surface adjacent the fabric edge to a margin of the second surface adjacent the fabric edge.

70. The implantable prosthesis according to claim 69, wherein the at least one fabric edge includes an opening edge that forms a portion of the opening, and wherein the at least one edge barrier includes an opening edge barrier that extends about the opening edge to inhibit the formation of adhesions between the opening edge and the tube-like structure.

71. The implantable prosthesis according to claim 68, wherein the at least one fabric edge includes an outer peripheral edge, and wherein the at least one edge barrier includes an outer edge barrier that extends about at least a portion of the outer peripheral edge to inhibit the formation of adhesions between the portion of the outer peripheral edge and adjacent tissue or organs.

72. The implantable prosthesis according to claim 68, wherein the at least one edge barrier is formed from ePTFE.

73. The implantable prosthesis according to claim 62, wherein each of the first and second segments has a partial annular shape.

74. The implantable prosthesis according to claim 73, wherein the prosthetic repair fabric has an ellipsoid shape with a major axis and a minor axis, the prosthetic repair fabric being asymmetric about the minor axis and including an oblate end and an acute end.

75. The implantable prosthesis according to claim 74, wherein the opening has a center that is located along the major axis and between the minor axis and the acute end.

76. The implantable prosthesis according to claim 62, wherein the layer of repair fabric has a plurality of interstices that are constructed and arranged to allow tissue ingrowth.

77. The implantable prosthesis according to claim 76, wherein the layer of repair fabric is formed from one of polypropylene mesh and PTFE mesh.

78. The implantable prosthesis according to claim 62, wherein the body portion is constructed and arranged to be placed proximate a patient's esophagus, the opening being adapted to receive the esophagus.

79. The implantable prosthesis according to claim 62, wherein the prosthetic repair fabric has a flat configuration.

80. An implantable prosthesis for repairing a tissue or muscle wall defect located near a tube-like structure, the implantable prosthesis comprising:

a prosthetic repair fabric having an opening that is adapted to receive the tube-like structure, the prosthetic repair fabric including first and second segments, each of the first and second segments including a layer of repair fabric that is susceptible to the formation of adhesions with tissue and organs and a surface barrier that inhibits the formation of adhesions with tissue and organs, the surface barrier being disposed on a surface of the layer of repair fabric, each of the first and second segments including a first end and a second end, the first end of the first segment overlapping the first end of the second segment at a first overlap area, the first overlap area being free of one of the layer of fabric and the surface barrier of at least one of the first and second segments.

81. The implantable prosthesis according to claim 80, wherein the first overlap area is free of the layer of fabric of one of the first and second segments.

82. The implantable prosthesis according to claim 81, wherein the first overlap area is free of the surface barrier of the other of the first and second segments.

83. The implantable prosthesis according to claim 80, wherein each of the first and second segments includes a surface barrier that inhibits the formation of adhesions with tissue and organs, the surface barrier being disposed on a surface of the layer of fabric to inhibit the formation of adhesions between the surface and adjacent tissue and organs when the implantable prosthesis is placed in a patient.

84. The implantable prosthesis according to claim 80, wherein each of the first and second segments includes at least one fabric edge, each of the first and second segments including at least one edge barrier that inhibits the formation of adhesions with tissue and organs, the at least one edge barrier extending about at least a portion of the at least one fabric edge to inhibit the formation of adhesions between the portion of the at least one fabric edge and adjacent tissue and organs.

85. The implantable prosthesis according to claim 84, wherein the at least one edge barrier includes a barrier layer that wraps about the at least one fabric edge from a margin of the first surface adjacent the fabric edge to a margin of the second surface adjacent the fabric edge.

86. The implantable prosthesis according to claim 85, wherein the at least one fabric edge includes an opening edge that forms a portion of the opening, and wherein the at least one edge barrier includes an opening edge barrier that extends about the opening edge to inhibit the formation of adhesions between the opening edge and the tube-like structure.

87. The implantable prosthesis according to claim 84, wherein the at least one fabric edge includes an outer peripheral edge, and wherein the at least one edge barrier includes an outer edge barrier that extends about at least a portion of the outer peripheral edge to inhibit the formation of adhesions between the portion of the outer peripheral edge and adjacent tissue or organs.

88. The implantable prosthesis according to claim 84, wherein the at least one edge barrier is formed from ePTFE.

89. The implantable prosthesis according to claim 80, wherein each of the first and second segments has a partial annular shape.

90. The implantable prosthesis according to claim 89, wherein the prosthetic repair fabric has an ellipsoid shape with a major axis and a minor axis, the prosthetic repair fabric being asymmetric about the minor axis and including an oblate end and an acute end.

91. The implantable prosthesis according to claim 90, wherein the opening has a center that is located along the major axis and between the minor axis and the acute end.

92. The implantable prosthesis according to claim 80, wherein the layer of repair fabric has a plurality of interstices that are constructed and arranged to allow tissue ingrowth.

93. The implantable prosthesis according to claim 92, wherein the layer of repair fabric is formed from one of polypropylene mesh and PTFE mesh.

94. The implantable prosthesis according to claim 80, wherein the surface barrier is formed from ePTFE.

95. The implantable prosthesis according to claim 80, wherein the body portion is constructed and arranged to be placed proximate a patient's esophagus, the opening being adapted to receive the esophagus.

96. The implantable prosthesis according to claim 80, wherein the prosthetic repair fabric has a flat configuration.

* * * * *